(12) United States Patent
Shunichirou

(10) Patent No.: US 6,454,628 B1
(45) Date of Patent: *Sep. 24, 2002

(54) GIRDLE FOR TREATMENT OF LUMBAGO

(76) Inventor: Ishii Shunichirou, 676, Oaza Sasai, Ogawa-machi, Higashiibaraki-gun, Ibaraki (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/971,124

(22) Filed: Oct. 5, 2001

(30) Foreign Application Priority Data

Sep. 13, 2001 (JP) ........................................ 2001-278230

(51) Int. Cl.[7] ................................................ A41D 13/00
(52) U.S. Cl. ..................... 450/155; 128/90.1; 128/96.1; 450/96
(58) Field of Search ................................ 450/155, 151, 450/94, 96–98, 115, 100, 101, 116, 127, 122, 123, 131, 128, 132, 125, 133; 128/90.1, 96.1, 99.1, 101.1, 100.1; 602/19; 2/44, 45, 310–312, 338, 237, 221, 76, 92, 400–408, 227, 228, 220.7

(56) References Cited

U.S. PATENT DOCUMENTS

| | | | | |
|---|---|---|---|---|
| 1,185,672 A | * | 6/1916 | Huettner | 450/155 |
| 1,572,826 A | * | 2/1926 | Virgen | 450/155 |
| 2,584,279 A | * | 2/1952 | McDowell | 450/155 |
| 3,454,003 A | * | 7/1969 | Kleber-Sailhen | 450/155 |
| 3,524,449 A | * | 8/1970 | Peters | 450/155 |
| 6,080,038 A | * | 6/2000 | Sano | 450/155 |
| 6,146,240 A | * | 11/2000 | Morris | 450/155 |
| 6,338,666 B1 | * | 1/2002 | Ishii | 450/97 |

* cited by examiner

Primary Examiner—Gloria M. Hale
(74) Attorney, Agent, or Firm—Armstrong, Westerman & Hattori, LLP

(57) ABSTRACT

A girdle includes: a main body including a press portion with a zipper extending to a crotch portion from a belt on an upper part of a front of the main body, a portion sewn on a back of the main body, a right and left femoral part, a left-engaging member disposed on a left side of the press portion, and a right-engaging member disposed on a right side of the press portion; a left band attached between a left end portion of the main body and a tip end of which a left engaging member is attached; a right band attached between a right end portion of the main body and a tip end of which a right engaging member is attached; the left band ascending toward the left, and the right band ascending toward the right.

12 Claims, 40 Drawing Sheets

GIRDLE FOR TREATMENT OF LUMBAGO

DETAILED DESCRIPTION OF THE INVENTION

1. Technical Field of the Invention

The present invention relates to an improvement of a lumbago treating girdle for relieving lumbago and easing one's lumbar.

2. Prior Art

There has heretofore been "Body Shaping Girdle" disclosed in Japanese Utility Model Registration Publication No. 2010866 and "Girdle" disclosed in Japanese Patent Application Laid-Open No. 8303/1998.

3. Problems to be Solved by the Invention

Additionally, examples of an object fitted with a conventional girdle include adults and children, that is, young and old of both sexes who have lumbago because of functional deterioration and damage of gluteus maximus muscle. Generally commercial girdles are only standard products having standard sizes such as LMS, and there is no girdle that can finely be adjusted to fit individual body types. Additionally, when a person has to put on the girdle all day long, or walk or act otherwise with the girdle on, the girdle deviates from a fitted position, and the person gains more serious lumbago again.

Moreover, particularly when a fat person with the girdle on sits down, the person's abdomen is doubly pressed by clothing, and girdle only whose abdominal part is adjustable, and the person feels remarkably uneasy and uncomfortable.

Furthermore, a main object of the conventional girdle is to shape the body, and there has been no girdle which is superior in function of treating lumbago in a short term, quickly handling the girdle, during urination, or raising one's buttock to provide a beauty effect that one's lower body looks beautiful.

Therefore, an object of the present invention is to provide a lumbago treating girdle which is superior in functions such that one can comfortably have the girdle on without any feeling of pressure, one's body is shaped, comprehensive medicine including prevention, cure, and rehabilitation is possible not only on a substantial lumbago part but also on one's entire lumbar to treat and completely cure the lumbago in a short term, convenience during urination is enhanced, and a beauty effect is produced to make one's lower body look remarkably beautiful.

4. Means for Solving the Problem

According to the present invention, there is provided a lumbago treating girdle comprising: a girdle main body including an inverse-triangular press portion provided with a zipper extending in a vertical direction to a crotch portion from a belt disposed on an upper part of a front surface of the girdle main body, a portion sewn in the vertical direction on a back surface, a right femoral part, a left femoral part, a left engaging member on the left side of the press portion and a right engaging member on the right side of the press portion; a left stretch band which is attached to a middle of a left end portion of the girdle main body, and to a tip end of which a left engaging member provided with an engaging piece attached to one surface thereof is attached; and a right stretch band which is attached to a middle of a right end portion of the girdle main body, and to a tip end of which a right engaging member provided with an engaging piece attached to one surface thereof is attached, the left stretch band being attached to the girdle main body in such a manner that the left stretch band ascends toward the left, and the right stretch band being attached to the girdle main body in such a manner that the right stretch band ascends toward the right.

[Embodiments]

A girdle for treatment for lumbago according to the present invention will be described in detail with reference to the accompanying drawings.

FIGS. 1 to 4 are views showing a first embodiment of the lumbago treating girdle of the present invention. FIG. 1 is a front view showing the first embodiment of the lumbago treating girdle according to the present invention before a stretch band is wound around the lumbago treating girdle, FIG. 2 is a back view of the lumbago treating girdle before the stretch band is wound therearound, FIG. 3 is a front view of the lumbago treating girdle after the stretch band is wound therearound, and FIG. 4 is a back view of the lumbago treating girdle after the stretch band is wound therearound.

As shown in FIG. 1, a lumbago treating girdle 1 of the present invention is constituted of: a girdle main body 2 having a right femoral part 5 in which a right leg passing port 5a for passing one's right-leg right femoral part is formed, and a left femoral part 6 in which a left leg passing port 6a for passing one's left-leg left femoral part is formed; and left and right stretch bands 3, 4 attached to left and right end portions of the girdle main body 2.

A material of the left and right stretch bands 3, 4 is, for example, an expandable/contractible material, such as rubber. Particularly, a meshed material superior in air permeability may be used for summer. Moreover, the expandable/contractible material is preferably used for winter. In this manner, the material can selectively be used in accordance with functions suitable for seasons.

A belt 11 is formed in an upper part of the girdle main body 2, and an entirely inverse triangular press portion 12 is formed to extend from the band 11 to a crotch portion 2a in a front surface of the girdle main body 2. In the inverse triangular press portion 12, a thick core is inserted, and surrounded with left and right seams 12a, 12b.

Left and right engaging members 3a, 4a are sewn and attached to tip ends of the left and right stretch bands 3, 4, or integrally formed on the tip ends of the left and right stretch bands 3, 4. Lower ends of the left and right seams 12a, 12b are connected to the crotch portion 2a.

As shown in FIG. 1, the belt 11 provided with a plurality of semicircular trimmings is attached to the upper part of the girdle main body 2, and a zipper 9 is attached to a middle portion of the inverse triangular press portion 12 in a vertical direction. Reference numeral 10 denotes an opening/closing metal piece for opening/closing the zipper 9.

Moreover, a left engaging member 7 formed substantially in a trapezoidal shape is attached to the left side of the left seam 12a of the press portion 12, and a right engaging member 8 is attached to the right side of the right seam 12b of the press portion 12. The stretch band 3 is attached substantially to a middle of a left end of the girdle main body 2, and the engaging member 3a formed substantially in a semicircular shape is attached to the tip end of the stretch band in such a manner that a left end of the engaging member 3a is tilted upward to the left. An engaging piece 3b is attached to a back surface of the engaging member 3a. The engaging piece 3b is attached only to the back surface.

Moreover, the stretch band 4 is attached substantially to a right end of the girdle main body 2, and the engaging member 4a formed substantially in the semicircular shape is attached to the tip end of the stretch band in such a manner that a right end of the engaging member 4a is tilted upward to the right. An engaging piece 4b is attached to the back surface of the engaging member 4a. Respective tip ends of the engaging members 3a, 4a are formed in circular shapes, and the engaging piece 4b is attached only to the back surface. The engaging members 3a, 4a are attached to the tip ends of the left and right stretch bands 3, 4 in such a manner that the respective tip ends of the engaging members are tilted upward to the left and right, that is, obliquely turn to an upward direction.

FIG. 2 is a back view showing the first embodiment of the lumbago treating girdle according to the-present invention before the stretch band is wound around girdle. As shown in FIG. 2, the left stretch band 3 is attached to the girdle main body 2 in such a manner that the tip end of the left stretch band 3 ascends toward the left. Moreover, the right stretch band 4 is attached to the girdle main body 2 in such a manner that the tip end of the right stretch band 4 slightly ascends toward the right. No press portion 12 is disposed in the back surface of the girdle main body 2, and a sewn portion 2b is disposed in the middle of the back surface to vertically extend downward to the crotch portion 2a from the belt 11 disposed in the upper part of the girdle main body 2.

Moreover, FIG. 3 is a front view showing the first embodiment of the lumbago treating girdle according to the present invention after the stretch band is wound around the girdle.

As shown in FIG. 3, the engaging piece 3b attached to the engaging member 3a attached to the tip end of the left stretch band 3 is joined to the left engaging member 7, and the engaging piece 4b attached to the right engaging member 4a is joined to the right engaging member 8. FIG. 4 is a back view showing the first embodiment of the lumbago treating girdle according to the present invention after the stretch band is wound around the girdle. The left and right stretch bands 3, 4 attached to the girdle main body 2 are crossed in an X shape and wound around the vicinity of the center of a buttock portion 2c of the back surface during use.

As shown in FIGS. 3, 4, when the engaging pieces 3b, 4b of the left and right engaging members 3a, 4a attached to the tip ends of the left and right stretch bands 3, 4 are joined to the left and right engaging members 7, 8 in slightly deviating positions, intensity of feeling of fitting of the stretch bands 3, 4 can be adjusted. When a fat person puts on the present lumbago treating girdle 1 and sits, the person's abdomen is pressed by the press portion 12 sewn onto the front surface of the girdle main body 2 with the seams 12a, 12b shown in FIG. 3. In this case, the press portion 12 spreads forward with the seams 12a, 12b for fine adjustment so that the person's abdomen is prevented from being pressed.

FIGS. 5 to 8 show a second embodiment of the lumbago treating girdle of the present invention. FIG. 5 is a front view showing the second embodiment of the lumbago treating girdle according to the present invention before the stretch band is wound around the girdle, FIG. 6 is a back view showing the second embodiment of the lumbago treating girdle according to the present invention before the stretch band is wound around the girdle, FIG. 7 is a front view showing the second embodiment of the lumbago treating girdle according to the present invention after the stretch band is wound around the girdle, and FIG. 8 is a back view showing the second embodiment of the lumbago treating girdle according to the present invention after the stretch band is wound around the girdle.

A lumbago treating girdle la of the second embodiment is largely different from the lumbago treating girdle 1 of the first embodiment in that the left or right engaging member 3a, 4a with the left or right engaging piece 3b, 3c attached to the back surface thereof is attached to tip ends of two left or right stretch bands 3, 4, instead of one left or right stretch band 3, 4.

That is to say, as shown in FIG. 5, left upper and lower stretch bands 3c, 3d are attached to the left end of the girdle main body 2 in such a manner that the tip ends of the bands slightly ascend toward the left. The left engaging member 3a with the engaging piece 3b attached to the back surface thereof is sewn and attached to the tip ends of the left upper and lower stretch bands 3c, 3d in such a manner that the tip end of the member slightly ascends toward the left.

Moreover, right upper and lower stretch bands 4c, 4d are attached to the right end of the girdle main body 2 in such a manner that the tip ends of the bands slightly ascend toward the right. The right engaging member 4a with the engaging piece 4b attached to the back surface thereof is sewn and attached to the tip ends of the right upper and lower stretch bands 4c, 4d in such a manner that the tip end of the member slightly ascends toward the right.

The other constitution of the lumbago treating girdle 1a of the second embodiment is the same as that of the lumbago treating girdle 1 of the first embodiment. As shown in FIGS. 5 to 8, since the right or left stretch band is formed of two upper and lower stretch bands 3c and 3d, or 4c and 4d, one's buttock can securely be pressed, pelvis is stabilized, and lumbago can be prevented. In the lumbago treating girdle 1a of the second embodiment, each of the left and right stretch bands 3, 4 is formed of two bands, but may be formed of three, or four bands, if necessary.

FIG. 9 is a front view showing a third embodiment of the lumbago treating girdle according to the present invention after the stretch band is wound around the girdle. A lumbago treating girdle 1b of the third embodiment is constituted by disposing an opening/closing portion 13 above the crotch portion 2a on the front surface of the girdle main body 2 of the lumbago treating girdle 1 described in the first embodiment. Moreover, the other constitution is the same as that of the lumbago treating girdle 1 of the first embodiment.

As shown in FIG. 9, since the opening/closing portion 13 is disposed right above the crotch portion 2a in the middle part of the girdle main body 2, this structure is convenient for a man with the lumbago treating girdle 1b thereon during urination.

FIG. 10 is a front view showing a fourth embodiment of the lumbago treating girdle according to the present invention after the a stretch band is wound around the girdle. A lumbago treating girdle 1c of the fourth embodiment is constituted by disposing the opening/closing portion 13 above the crotch portion 2a on the front surface of the girdle main body 2 of the lumbago treating girdle 1a described in the second embodiment. Moreover, the other constitution is the same as that of the lumbago treating girdle 1a of the second embodiment.

As shown in FIG. 10, the opening/closing portion 13 is disposed right above the crotch portion 2a in the middle part of the girdle main body 2. Therefore, when a man puts on the lumbago treating girdle 1c, urination is facilitated. FIG. 11 is a longitudinal sectional view of the opening/closing portion disposed in the third and fourth embodiments of the lumbago treating girdle according to the present invention, and FIG. 12 is a longitudinal sectional view of another example of the opening/closing portion disposed in the third and fourth embodiments of the lumbago treating girdle according to the present invention.

As shown in FIG. 11, the opening/closing portion 13 is constituted of a lower opening/closing piece 14 and an upper opening/closing piece 15 attached to the girdle main body 2. An engaging portion 14a is attached to an outer surface of the lower opening/closing piece 14, and an engaging portion 15a is attached to an inner surface of a lower end of the upper opening/closing piece 15. In the opening/closing portion 13, the upper opening/closing piece 15 is positioned outside the lower opening/closing piece 14.

An opening/closing portion 13a shown in FIG. 12 is different in structure from the opening/closing portion 13 shown in FIG. 11. That is to say, in the opening/closing portion 13a of the present example, the engaging portion 14a is attached to the inner surface of the upper end of the lower opening/closing piece 14, and the engaging portion 15a is attached to the outer surface of the lower end of the upper opening/closing piece 15. Moreover, the lower end of the upper opening/closing piece 15 is positioned inside, the upper end of the lower opening/closing piece 14 is positioned outside, and the engaging portion 15a of the upper opening/closing piece 15 engages with the engaging portion 14a of the lower opening/closing piece 14. The engaging portion 14a of the lower opening/closing piece 14 is detachably attached to the engaging portion 15a of the upper opening/closing piece 15.

FIG. 13 is a back view showing a fifth embodiment of the lumbago treating girdle according to the present invention before the stretch band is wound around the girdle. A lumbago treating girdle 1d of the fifth embodiment is constituted by disposing a cross band portion 16 on the back surface of the girdle main body 2 of the lumbago treating girdle 1 of the first embodiment shown in FIGS. 1 to 4.

As shown in FIG. 13, in the lumbago treating girdle 1d of the fifth embodiment, the cross band portion 16 is constituted of: a left cross band 16a whose one end is sewn to the left femoral part 6 of the girdle main body 2; a right cross band 16b whose one end is sewn to the right femoral part 5 of the girdle main body 2; and left and right engaging members 17, 17a for engaging with the other ends of the left and right cross bands 16a, 16b.

For the left cross band 16a, one end of the left cross band 16a is sewn to the left femoral part 6 so as to ascend toward the right, and one end of the right cross band 16b is sewn to the right femoral part 5 so as to ascend toward the left. Moreover, the left and right engaging members 17, 17a are attached to predetermined positions of the upper part of the back surface of the girdle main body 2, with which the tip ends of the left and right cross bands 16a, 16b can engage. When the tip end of the left cross band 16a is joined to the right engaging member 17a and the tip end of the right cross band 16b is joined to the left engaging member 17 in a wrapped manner, the left and right cross bands 16a, 16b cross each other in an X shape.

FIG. 14 is a longitudinal sectional view of the cross band of the fifth embodiment of the lumbago treating girdle according to the present invention. As shown in FIG. 14, one end of the left or right cross band 16a, 16b is sewn to the back surface of the girdle main body 2, and the other end (tip end) thereof is provided with an engaging portion 18, 18a.

On the back surface of the girdle main body 2, the left and right engaging members 17, 17a attached to the positions with which the tip ends of the left and right cross bands 16a, 16b can engage have U-shaped sectional shapes, and lower engaging pieces 17b, 17c constituting the U-shaped left and right engaging members 17, 17a are sewn to the back surface of the girdle main body 2. On the inner surfaces of upper engaging pieces 17d, 17e and the upper surface of the lower engaging pieces 17b, 17e constituting the left and right engaging members 17, 17a, engaging portions for engaging with the engaging portions 18, 18a attached to the tip ends of the left and right cross bands 16a, 16b are attached.

In FIG. 14, as shown by dotted lines, the upper engaging pieces 17d, 17e can be raised/lowered. In this manner, the tip ends of the left and right cross bands 16, 16b can be held and joined into the U-shaped left and right engaging members 17, 17a in the wrapped manner. The cross band portion 16 may be attached to the back surface of the girdle main body 2 of the lumbago treating girdle 1a of the second embodiment according to the present invention.

FIGS. 15 to 17 show a sixth embodiment of the lumbago treating girdle according to the present invention. FIG. 15 is a back view showing the sixth embodiment of the lumbago treating girdle according to the present invention before the stretch band is wound around the girdle, FIG. 16 is a longitudinal sectional view of a horizontal band of the sixth embodiment of the lumbago treating girdle according to the present invention, and FIG. 17 is a longitudinal sectional view of another example of the horizontal band disposed in the sixth embodiment of the lumbago treating girdle according to the present invention.

As shown in FIG. 15, a lumbago treating girdle 1e of the sixth embodiment is a lumbago treating girdle in which a horizontal band portion 19 is disposed on the back surface of the girdle main body 2 of the lumbago treating girdle 1 according to the first embodiment shown in FIGS. 1 to 4. For the lumbago treating girdle 1e of the sixth embodiment, as shown in FIG. 15, the horizontal band portion 19 is constituted of: a horizontal band 19a with engaging portions 21, 21a attached to left and right end portions thereof; and left and right engaging members 20, 20a, attached to left and right positions of substantially the middle part of the back surface of the girdle main body 2, for engaging with the horizontal band 19a.

The left and right engaging members 20, 20a are attached to the back surface of the horizontal band 19a of the horizontal band portion 19 such that the engaging members are substantially linearly aligned with the left and right stretch bands 3, 4. As shown in FIG. 16, the left and right engaging members 20, 20a of the horizontal band portion 19 attached to the middle part of the back surface of the girdle main body 2 have a U-shaped longitudinal section, and upper engaging pieces 20d, 20e are connected to lower engaging pieces 20b, 20c.

Engaging portions 20f, 20g are attached to between the upper engaging pieces 20d, 20e and the lower engaging pieces 20b, 20c of the left and right engaging members 20, 20a, and engaging portions 19b, 19c attached to left and right ends of the horizontal band 19a engage with the engaging portions 20f, 20g, so that the horizontal band 19a can be detachably attached to between the left and right engaging members 20 and 20a.

As shown in FIG. 17, instead of the U-shaped left and right engaging members 22, 22a, flat left and right engaging members 22, 22a are attached to the back surface of the girdle main body 2, and engaging portions 22b, 22c may be attached to upper surfaces of the engaging members. The horizontal band 19a is detachably attached to between the left and right engaging members 22 and 22a. In FIG. 15, one stretch band 3, 4 with the engaging member 3a, 4a sewn thereto is disposed on either one side, but instead of one horizontal band 19a, a plurality of horizontal bands may be detachably attached to the horizontal band portion 19.

FIG. 18 is a back view showing a seventh embodiment of the lumbago treating girdle according to the present invention before the stretch band is wound around the girdle. As shown in FIG. 18, in a lumbago treating girdle 1f of the seventh embodiment, an H-shaped shaping member 23 is sewn onto a back inner surface of the girdle main body 2.

The lumbago treating girdle 1f of the seventh embodiment is constituted by sewing the H-shaped shaping member 23 onto the back inner surface of the girdle main body 2 of the lumbago treating girdle 1 of the first embodiment. Of course, the H-shaped shaping member 23 may be sewn onto a back outer surface of the girdle main body 2. The shaping member 23 is constituted of a left vertical piece 23a, right vertical piece 23b and horizontal piece 23c. The horizontal piece 23c is disposed substantially in a middle between the left and right vertical pieces 23a and 23b.

In order to sew the shaping member 23 onto the back inner surface of the girdle main body 2, the left vertical piece 23a of the shaping member 23 is sewn onto the left end of the inner surface of the girdle main body 2, the right vertical piece 23b is sewn onto the right end of the inner surface of the girdle main body 2, and the horizontal piece 23c is sewn substantially onto the inner surface of the crotch portion 2a. The H-shaped shaping member 23 is sewn onto the back inner surface of the girdle main body in this manner. Therefore, when one puts on the lumbago treating girdle 1f of the seventh embodiment, one's lumbar, buttock, femur, and the like can be shaped. The H-shaped shaping member 23 is sewn onto the inner surface. Therefore, even when one puts on the girdle, appearance is good, and one's lower body can look beautiful. It can be expected that especially women like to use this type of lumbago treating girdle.

FIG. 19 is a back view showing an eighth embodiment of the lumbago treating girdle according to the present invention before the stretch band is wound around the girdle. As shown in FIG. 19, in a lumbago treating girdle 1f of the eighth embodiment, the H-shaped shaping member 23 is sewn onto the back inner surface of the girdle main body 2. The lumbago treating girdle 1f of the eighth embodiment is constituted by sewing the H-shaped shaping member 23 to the back inner surface of the girdle main body 2 of the lumbago treating girdle 1a of the second embodiment.

Of course, the H-shaped shaping member 23 may be sewn to the back outer surface of the girdle main body 2. The shaping member 23 is constituted of the left vertical piece 23a, right vertical piece 23b and horizontal piece 23c. The horizontal piece 23c is disposed substantially in the middle between the left and right vertical pieces 23a and 23b. In order to sew the shaping member 23 onto the back inner surface of the girdle main body 2, the left vertical piece 23a of the shaping member 23 is sewn onto the left end of the inner surface of the girdle main body 2, the right vertical piece 23b is sewn onto the right end of the inner surface of the girdle main body 2, and the horizontal piece 23c is sewn substantially onto the inner surface of the crotch portion 2a.

The H-shaped shaping member 23 is sewn onto the back inner surface of the girdle main body in this manner. Therefore, when one puts on the lumbago treating girdle 1f of the eighth embodiment, one's lumbar, buttock, femur, and the like can be shaped. The Hshaped shaping member 23 is sewn onto the inner surface of the girdle main body. Therefore, even when one puts on the girdle, appearance is good, and one's lower body can look beautiful. It can be expected that especially women like to use this type of lumbago treating girdle.

The H-shaped shaping member 23 may be sewn onto the lumbago treating girdles 1 to 1e of the first to seventh embodiments.

FIG. 20 is a front view showing a ninth embodiment of the lumbago treating girdle according to the present invention before the stretch band is wound around the main body of the girdle, FIG. 21 is a back view of the lumbago treating girdle according to the present embodiment before the stretch band is wound around the main body of the girdle, FIG. 22 is a front view of the lumbago treating girdle according to the present embodiment after the stretch band is wound around the main body of the girdle, and FIG. 23 is a back view of the lumbago treating-girdle according to the present embodiment after the stretch band is wound around the main body of the girdle.

As shown in FIG. 20, a lumbago treating girdle 1h of the present embodiment is constituted of: a main body 2 of the lumbago treating girdle 1h, having the right femoral part 5 in which the right leg passing port 5a for passing one's right-leg right femoral part is formed, and the left femoral part 6 in which the left leg passing port 6a for passing one's left-leg left femoral part is formed; and the left and right stretch bands 3, 4 attached to the left and right end portions of the girdle main body 2.

The material of the left and right stretch bands 3, 4 is, for example, an expandable/contractible material, such as rubber. Particularly, a meshed material superior in air permeability may be used for summer. Moreover, the expandable/contractible material is preferably used for winter. In this manner, the material can selectively be used in accordance with functions suitable for seasons.

In the materials of the left and right stretch bands 3, 4 attached to the main body 2 of the lumbago treating girdle 1h according to the present embodiment, stretch portions 3i, 4i and mesh portions 3j, 4j are alternately knitted.

Each of the stretch portions 3i, 4i has a thickness of about 2 mm, and each of the mesh portions 3j, 4j has a thickness of about 1 mm. The mesh portions 3j, 4j are processed in mesh forms and a large number of holes are formed in the portions particularly in order to enhance the air permeability. In this manner, the stretch bands 3, 4 of the lumbago treating girdle 1h according to the present embodiment are remarkably superior in expandable/contractible properties and air permeability, and are additionally thin. Therefore, even if one puts on the girdle, a body part with the girdle attached thereto is never deformed.

The belt 11 is formed in the upper part of the girdle main body 2, and the entirely inverse triangular press portion 12 is formed to extend from the band 11 to the crotch portion 2a in the front surface of the girdle main body 2. In the inverse triangular press portion 12, a thick core is inserted, and surrounded with left and right seams 12a, 12b on left and right sides of the portion.

The left and right engaging members 3a, 4a are sewn and attached to the tip ends of the left and right stretch bands 3, 4, or integrally formed on the tip ends of the left and right stretch bands 3, 4. The lower ends of the left and right seams 12a, 12b are connected to the crotch portion 2a.

As shown in FIG. 20, the belt 11 having a plurality of semicircular trimmings is attached to the upper part of the girdle main body 2, and the zipper 9 having the opening/closing metal piece 10 in the vertical direction is attached to the middle portion of the inverse triangular press portion 12.

The left stretch band 3, whose tip end is formed substantially in a semicircular shape and has a hemming member 3e sewn thereto, is attached to substantially the middle of the left end of the girdle main body 2 in such a manner that the tip end of the band is tilted upward to the left. Moreover, U-shaped female engagement metal pieces 3f, 3f are attached to the tip end of the left stretch band 3. The hemming member 3e is attached in order to shape the tip end of the stretch band 3 and to prevent the tip end from being deformed.

Moreover, the right stretch band 4, whose tip end is formed substantially in a trapezoidal shape and has a hemming member 4e sewn thereto, is attached to the right end of the girdle main body 2 in such a manner that the tip end of the left stretch band 4 is tilted upward to the right. As shown in FIG. 21, engaging pieces 4f, 4f are positioned on the back surface of the right stretch band 4. The engaging pieces 4f, 4f are attached to the back surface of the right stretch band 4.

FIG. 21 is a back view of the lumbago treating girdle according to the present embodiment. As shown in FIG. 20, the engaging metal pieces 4f, 4f are attached to the back surface of the tip end of the right stretch band 4 of the lumbago treating girdle 1h according to the present embodiment at a predetermined interval. The engagement metal pieces 3f, 3f attached to the tip end of the left stretch band 3 are joined to the engaging metal pieces 4f, 4f.

In the lumbago treating girdle 1h of the present embodiment, the press portion 12 is not disposed in the back surface of the main body 2. A sewn portion 2b is disposed in the middle and extends downwards in the vertical direction to the crotch portion 2a from the belt 11 formed on the upper part of the main body 2.

As shown in FIG. 21, the lumbago treating girdle 1h of the present embodiment is constituted such that an H-shaped shaping member 23 is sewn to an inner back side surface of the girdle main body 2. Of course, the shaping member 23 formed in the H-shape may be sewn to a front outer surface of the girdle main body 2. The shaping member 23 is constituted of a left vertical piece 23a, a right vertical piece 23b, and a horizontal piece 23c.

The horizontal piece 23c is disposed substantially in the middle between the left vertical piece 23a and the right vertical piece 23b. In order to sew and attach the shaping member 23 to the back inner side surface of the girdle main body 2, the left vertical piece 23a of the shaping member 23 is sewn to the left end of the inner side surface of the girdle main body 2, the right vertical piece 23b is sewn to the right end of the inner side surface of the girdle main body 2, and the horizontal piece 23c is sewn substantially to the inner side surface of the crotch portion 2a.

The shaping member 23 formed in the H-shape is sewn to the back inner side surface in this manner. When one puts on the lumbago treating girdle 1h of the present embodiment, one's back, buttocks, thigh, and the like can be shaped. Since the H-shaped shaping member 23 is sewn to the inner side surface, the girdle even put on the body looks nice, a lower part of the body can be allowed to look remarkably beautifully, and therefore the girdle can be expected to be used by women.

FIG. 22 is a front view showing that the stretch band of the lumbago treating girdle of the present embodiment is wound around the main body. As shown in FIG. 22, when the engagement metal pieces 3f, 3f attached to the tip end of the left stretch band 3 is joined to the engaging metal pieces 4f, 4f attached to the tip end of the right stretch band just before the zipper 9, the left stretch band 3 is connected to the right stretch band 4.

FIG. 23 is a back view showing that the left and right stretch bands of the lumbago treating girdle according to the present embodiment are wound. The left and right stretch bands 3, 4 attached to the girdle main body 2 are crossed in an X shape in the vicinity of the center of the buttock portion 2c of the back surface of the girdle main body 2 when wound around.

When a fat person puts on, uses, and sits with the present lumbago treating girdle oh including the press portion 12 sewn onto the front surface of the girdle main body 2 with the seams 12a, 12b shown in FIG. 20 and 21, the press portion 12 spreads forward with the seams 12a, 12b for fine adjustment in order to prevent the person's abdomen from being pressed.

FIG. 24 is a front view showing a tenth embodiment of the lumbago treating girdle according to the present invention before the stretch band is wound around the girdle, FIG. 25 is a back view of the lumbago treating girdle according to the present embodiment before the stretch band is wound around the girdle, FIG. 26 is a front view of the lumbago treating girdle according to the present embodiment after the stretch band is wound around the girdle, and FIG. 27 is a back view of the lumbago treating girdle according to the present embodiment after the stretch band is wound around the girdle.

In a lumbago treating girdle 1i of the tenth embodiment, a constitution of the girdle main body 2 is the same as that of the ninth embodiment. A different respect is that the left engaging member 7 formed substantially in a trapezoidal shape is attached to the left side of the left seam 12a of the press portion 12, and that the right engaging member 8 is attached to the right side of the right seam 12b of the press portion 12.

The left stretch band 3 whose tip end is formed substantially in the semicircular shape is attached substantially to the middle of the left end of the girdle main body 2 in such a manner that the tip end ascends toward the left. Moreover, the right stretch band 4 whose tip end is formed substantially in the semicircular shape is attached substantially to the middle of the right end of the girdle main body 2 in such a manner that the tip end ascends toward the right.

Furthermore, the hemming members 3e, 4e are disposed on the tip ends of the left and right stretch bands 3, 4. The hemming members 3e, 4e disposed on the tip ends prevent tip-end shapes from being deformed after continuous use. In the left and right stretch bands 3, 4, the stretch portions and mesh portions are alternately knitted, the stretch portion 3i or 4i has a thickness of about 2 mm, and the mesh portion 3j or 4j has a thickness of about 1 mm. The mesh portions 3j, 4j are processed in the mesh forms and a large number of holes are formed in the portions particularly in order to enhance the air permeability.

Through holes 3g, 4g having rectangular shapes are formed to be laterally long in the tip ends of the left and right stretch bands 3 and 4. Since the through holes 3g, 4g are formed in the tip ends of the left and right stretch bands 3, 4, attachment/detachment is facilitated.

As shown in FIG. 25, the shaping member 23 formed in the H-shape is attached to the back inner surface of the lumbago treating girdle 1i of the present embodiment. The left engaging piece 3b is attached to the back surface of the tip end of the left stretch band 3, and the right engaging piece 4b is attached to the back surface of the tip end of the right stretch band 4. The rectangular through holes 3g, 4g are formed to be laterally long in the middle of the left and right engaging pieces 4b, 4b.

Slip preventing members 24, 24 are attached to a base portion of the stretch band 3 in the vicinity of the left end of the girdle main body 2 and the base portion of the left stretch band 4 in the vicinity of the right end of the girdle main body 2. Since the slip preventing members 24, 24 are attached to the base portions of the left and right stretch bands 3, 4, the lumbago treating girdle 1i even put on the human body does not deviate. As shown in FIG. 26, the right engaging piece 4b attached to the back surface of the right stretch band 4 is joined to the left engaging member 7, and the left engaging piece 3b attached to the back surface of the left stretch band 3 is joined to the right engaging member 8. As shown in FIG. 27, the left and right stretch bands 3, 4 attached to the girdle main body 2 are crossed in the X shape in the vicinity of the center of the buttock portion 2c of the back surface of the girdle main body 2 when wound around for use.

FIG. 28 is a front view showing an eleventh embodiment of the lumbago treating girdle according to the present invention before the stretch band is wound around the main body, FIG. 29 is a back view of the lumbago treating girdle according to the present embodiment before the stretch band is wound around the main body, FIG. 30 is a front view of the lumbago treating girdle according to the present embodiment after the stretch band is wound around the main body, and FIG. 31 is a back view of the lumbago treating girdle according to the present embodiment after the stretch band is wound around the main body.

In a lumbago treating girdle 1j of the present embodiment, the constitution of the girdle main body 2 is the same as that of the girdle main body 2 of the tenth embodiment shown in FIG. 24. A constitution of the lumbago treating girdle 1j of the eleventh embodiment which is largely different from that of the lumbago treating girdle 1i of the tenth embodiment lies in the left and right stretch bands 3, 4. Moreover, attached position and state, and the like of the left and right stretch bands 3, 4 to the girdle main body 2 are the same as the attached position and state, and the like of the lumbago treating girdles 1h, 1i of the ninth and tenth embodiments.

As shown in FIG. 28, the tip ends of the left and right stretch bands 3, 4 of the lumbago treating girdle 1j of the present embodiment are formed substantially in the semi-circular shapes, and the hemming members 3e, 4e are attached to the tip ends of the left and right stretch bands 3, 4 in a surrounding manner. Moreover, as shown in FIG. 30, the left and right engaging pieces 3b, 4b attached to the back surfaces of the tip ends of the left and right stretch bands 3, 4 are joined to the left and right engaging members 7, 8.

As shown in FIG. 29, in the left and right stretch bands 3, 4, the stretch portions and mesh portions are alternately knitted, the stretch portion 3i or 4i has a thickness of about 2 mm, and the mesh portion 3j or 4j has a thickness of about 1 mm. The mesh portions 3j, 4j are processed in the mesh forms and a large number of holes are formed in the portions particularly in order to enhance the air permeability. Moreover, as shown in FIG. 31, the left and right stretch bands 3, 4 attached to the girdle main body 2 are crossed in the X shape in the vicinity of the center of the buttock portion 2c of the back surface of the girdle main body 2 when wound around for use.

In the lumbago treating girdle 1j of the present embodiment, base portions 3h, 4h of the left and right stretch bands 3, 4 in the vicinity of the girdle main body 2 are sewn to the back surface of the girdle main body 2. Since the base portions 3h, 4h are sewn/attached in this manner, the lumbago treating girdle 1j of the present embodiment can easily be put on the body.

FIG. 32 is a front view showing a twelfth embodiment of the lumbago treating girdle according to the present invention before the stretch band is wound around the main body, FIG. 33 is a back view of the lumbago treating girdle according to the present embodiment before the stretch band is wound around the main body, FIG. 34 is a front view of the lumbago treating girdle according to the present embodiment after the stretch band is wound around the main body, and FIG. 35 is a back view of the lumbago treating girdle according to the present embodiment after the stretch band is wound around the main body.

In a lumbago treating girdle 1k of the present embodiment, the constitution of the girdle main body 2 is the same as that of the girdle main body 2 of the tenth embodiment. As a different constitution, the left and right engaging members 7, 8 are formed in larger shapes. That is, the members are attached so as to cover even the left and right ends of the band 11 and the left and right seams 12a, 12b. The left and right engaging members 7, 8 have substantially the trapezoidal shapes.

Moreover, the largely different constitution of the lumbago treating girdle 1k of the present embodiment lies in the left and right stretch bands 3, 4. That is, the left stretch band 3 is constituted of an upper stretch band 3c and a lower stretch band 3d, and the hemming member 3e is attached to the tip ends of the upper and lower stretch bands 3c, 3d and extends continuously along the upper and lower stretch bands 3c, 3d. Furthermore, the left stretch band 3 is attached to the main body 2 so that the tip end of the band ascends leftwards, and the right stretch band 4 is attached to the main body 2 so that the tip end of the band ascends rightwards.

As shown in FIG. 33, the left and right engaging pieces 3b, 4b which are surrounded by the hemming members 3e, 4e and are forked into two parts are attached to the back surfaces of the tip ends of the left and right stretch bands 3, 4. As shown in FIG. 32, the stretch portions and mesh portions are alternately knitted in the left and right stretch bands 3, 4, the stretch portion 3i or 4i has a thickness of about 2 mm, and the mesh portion 3j or 4j has a thickness of about 1 mm. The mesh portions 3j, 4j are processed in the mesh forms and a large number of holes are formed in the portions particularly in order to enhance the air permeability.

The constitution of the lumbago treating girdle 1j of the present embodiment is largely different from that of the lumbago treating girdle 1i of the tenth embodiment in the left and right stretch bands 3, 4. Moreover, the attached states of the left and right stretch bands 3, 4 to the girdle main body 2 are the same as those of the ninth and tenth embodiments.

As shown in FIG. 34, the tip ends of the left and right stretch bands 3, 4 of the lumbago treating girdle 1k of the present embodiment are each formed into two parts, and the left and right engaging pieces 3b, 4b attached to the back surfaces of the tip ends of the left and right stretch bands 3, 4 are joined to the left and right engaging members 7, 8 of the girdle main body 2.

As shown in FIG. 35, the left and right stretch bands 3, 4 attached to the girdle main body 2 are crossed in the X shape in the vicinity of the center of the buttock portion 2c of the back surface of the girdle main body 2 when wound around for use. Even in the lumbago treating girdle 1k of the present embodiment, the slip preventing members may be attached to the base portions 3h, 4h of the stretch bands 3, 4 in the vicinity of the girdle main body 2.

FIG. 36 is a front view showing a thirteenth embodiment of the lumbago treating girdle according to the present invention before the stretch band is wound around the main body, FIG. 37 is a back view of the lumbago treating girdle according to the present embodiment before the stretch band is wound around the main body, and FIG. 38 is a front view of the lumbago treating girdle according to the present embodiment after the stretch band is wound around the main body.

As shown in FIG. 36, in a lumbago treating girdle 11 of the present embodiment, the constitution of the girdle main body 2 is the same as that of the girdle main body 2 of the tenth embodiment. The stretch portions and mesh portions are alternately knitted in the left and right stretch bands 3, 4, the stretch portion 3i or 4i has a thickness of about 2 mm, and the mesh portion 3j or 4j has a thickness of about 1 mm. The mesh portions 3j, 4j are processed in the mesh forms and a large number of holes are formed in the portions particularly in order to enhance the air permeability.

The constitution of the lumbago treating girdle 11 of the present embodiment largely different from the constitutions of the other embodiments lies in the left and right stretch bands 3, 4, as shown in FIG. 36. That is, concave portions are formed in middle portions of the tip ends of the left and right stretch bands 3, 4 and the tip ends are constituted to be formed into two forked parts.

As shown in FIG. 37, the left and right engaging pieces 3b, 4b which are surrounded by the hemming members 3e, 4e and which are each integrally formed in the two forked parts are attached to the back surfaces of the tip ends of the left and right stretch bands 3, 4 formed in the two forked parts.

The lumbago treating girdle 1l of the present embodiment is largely different from the lumbago treating girdle 1i of the twelfth embodiment in that the tip end of each of the left and right stretch bands 3, 4 is integrally formed in the two forked parts. Moreover, the attached state of the left and right stretch bands 3, 4 to the girdle main body 2 is also the same as that of the tenth embodiment.

As shown in FIG. 38, the tip end of each of the left and right stretch bands 3, 4 of the lumbago treating girdle 1l of the present embodiment is integrally formed in two forked parts, and the left and right engaging pieces 3b, 4b attached to the back surfaces of the tip ends of the left and right stretch bands 3, 4 are joined to the left and right engaging members 7, 8 of the girdle main body 2.

The left and right stretch bands 3, 4 attached to the girdle main body 2 are crossed in the X shape in the vicinity of the center of the buttock portion 2c of the back surface of the girdle main body 2 when wound around for use. Even in the lumbago treating girdle 1l of the present embodiment, the slip preventing members may be attached to the base portions 3h, 4h of the stretch bands 3, 4 in the vicinity of the girdle main body 2. The slip preventing members may be attached to the lumbago treating girdles 1 to 1l of all the embodiments according to the present invention.

FIGS. 39 and 40 are diagrams showing other embodiments of the stretch band of the lumbago treating girdle according to the present invention. The left and right stretch bands 3, 4 may be structured such that the tip ends of the left and right stretch bands to be attached to the lumbago treating girdles according to the first to thirteenth embodiments are formed in circular shapes, and circular through holes are formed in the left and right engaging pieces.

Moreover, as shown in FIG. 40, for the stretch band of the present embodiment, the left and right stretch bands 3, 4 may be constituted such that the tip ends of the left and right stretch bands to be attached to the lumbago treating girdles according to the first to thirteenth embodiments are formed in the two forked parts, and the left and right engaging pieces formed in the two forked parts are attached.

As shown in FIGS. 39 and 40, in the left and right stretch bands 3, 4 according to the embodiments of the lumbago treating girdles 1h to 1l of the present invention, the stretch portion 3i (4i) and mesh portion 3j (4j) are alternately arranged and knitted. A large number of small holes are formed in the mesh portion 3j (4j) in order to enhance the air permeability. Moreover, the thickness of the stretch portion 3i(4i) is in a range of 1 mm to 2 mm, and a material superior in expandable/contractible properties is used in the stretch portion. The material of the mesh portion 3j (4j) also has expandable/contractible properties, the thickness of the portion is about 1 mm, and the portion is remarkably excellent in the air permeability.

The zipper 9 having the opening/closing metal piece 10 is attached to the girdle main body 2 according to the embodiments of the lumbago treating girdles 1 to 1l of the present invention, but the zipper 9 having the opening/closing metal piece 10 may not be attached to the structure.

That is, the girdle main bodies 2 of FIGS. 1, 3, 3, 5, 7, 9, 10, 20, 22, 24, 26, 28, 30, 32, 34, 36 and 38 showing the lumbago treating girdles 1 to 1l according to the present invention may be structured such that the zipper 9 having the opening/closing metal piece 10 is not attached.

Advantages of the Invention

Since the present invention is constituted as described above, the following effects can be obtained. First, the present girdle for treatment provides no feeling of pressure because of the V-shaped seam and inverse-triangular press portion disposed on the main body.

Secondly, one or two wide left and right stretch bands of the present lumbago treating girdle are crossed at the buttock part and attached to the vicinity of the femoral parts of the front surface, or the stretch bands can be attached to the back surface in the X shape or the horizontal shape so that the stretch bands can finely be adjusted. Therefore, a balance between left and right pelvis parts is enhanced, gluteus maximus muscle is strengthened, comprehensive medicine including prevention, cure and rehabilitation is performed on the entire lumbar, and lumbago can be treated and completely cured in a relative short term.

Thirdly, in the present lumbago treating girdle, an outer periphery of upper and lower engaging members is sewn to form the middle overlapped portion. Therefore, men can quickly and easily open the girdle during urination.

Fourthly, since push-up materials having no stretching properties are sewn into the left and right side surfaces, front middle surface, and back middle surface of the present lumbago treating girdle, there can be provided the lumbago treating girdle functionally superior in a beauty effect that one's lower body looks remarkably beautiful.

Fifthly, stretch bands of the present lumbago treating girdle are very thin and constituted to be remarkably excellent in the air permeability. Therefore, even if one puts on the girdle, there can't be provided the thickness of the stretch band from the appearance. Additionally, even if one puts on the girdle in summer, one doesn't become hot.

Figure 1:
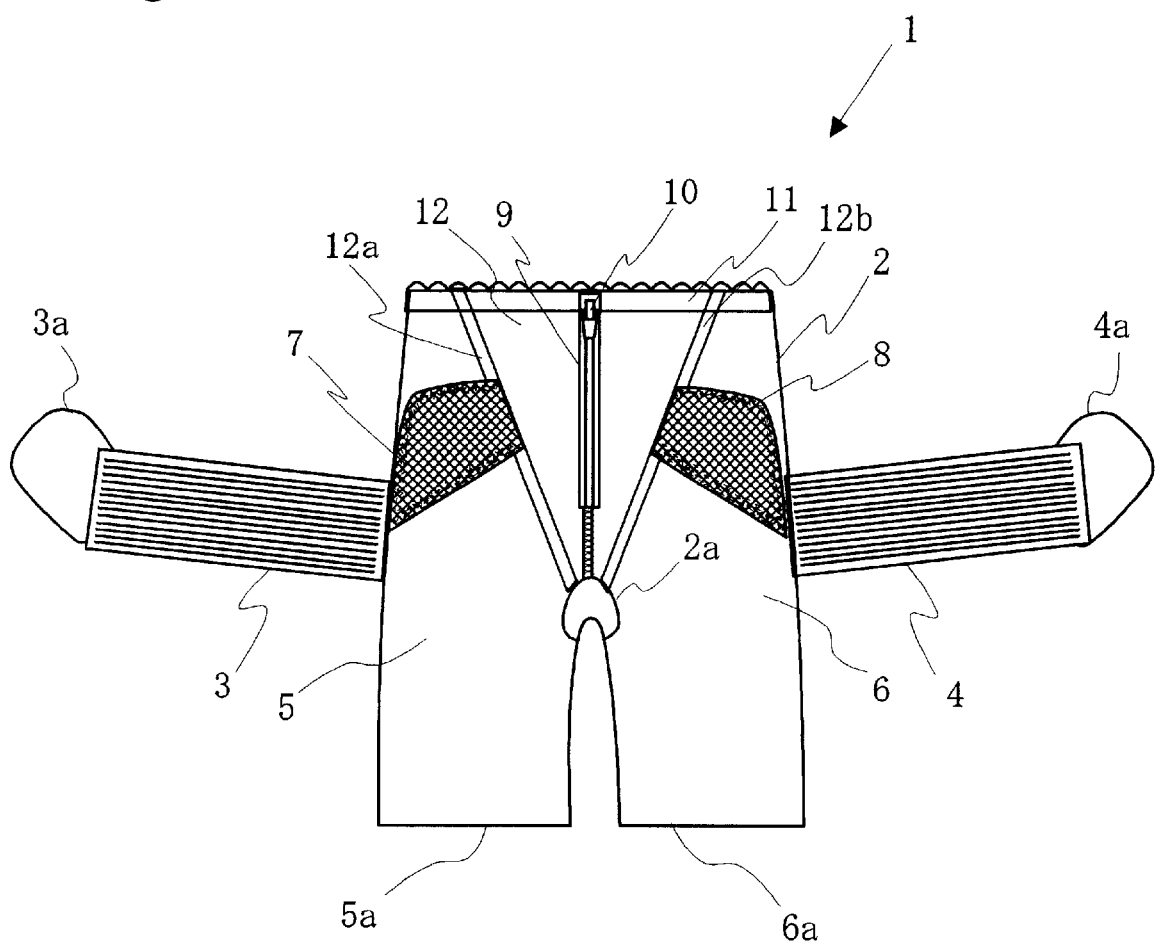
FIG. 1 is a front view showing the first embodiment of a lumbago treating girdle according to the present invention before a stretch band is wound around the lumbago treating girdle.
Figure 2:
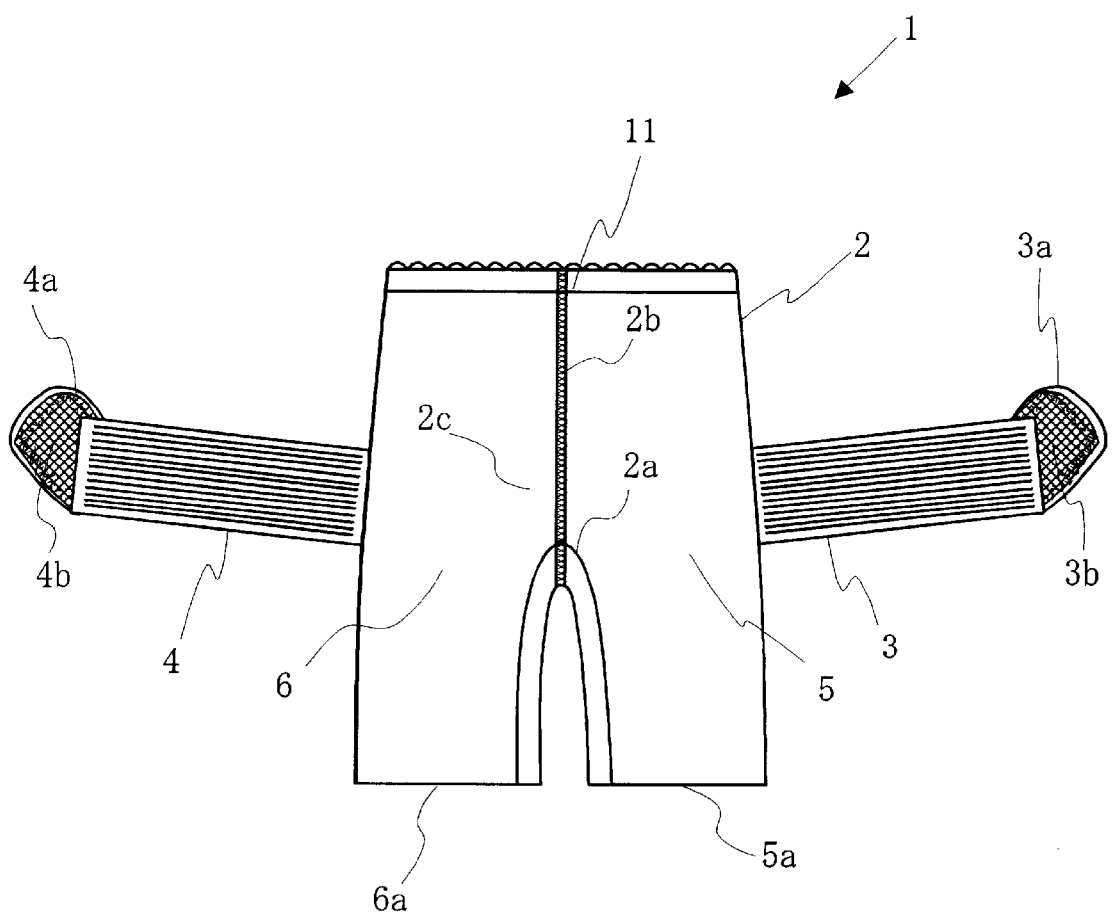
FIG. 2 is a back view showing the first embodiment of the lumbago treating girdle according to the present invention before the stretch band is wound therearound.
Figure 3:
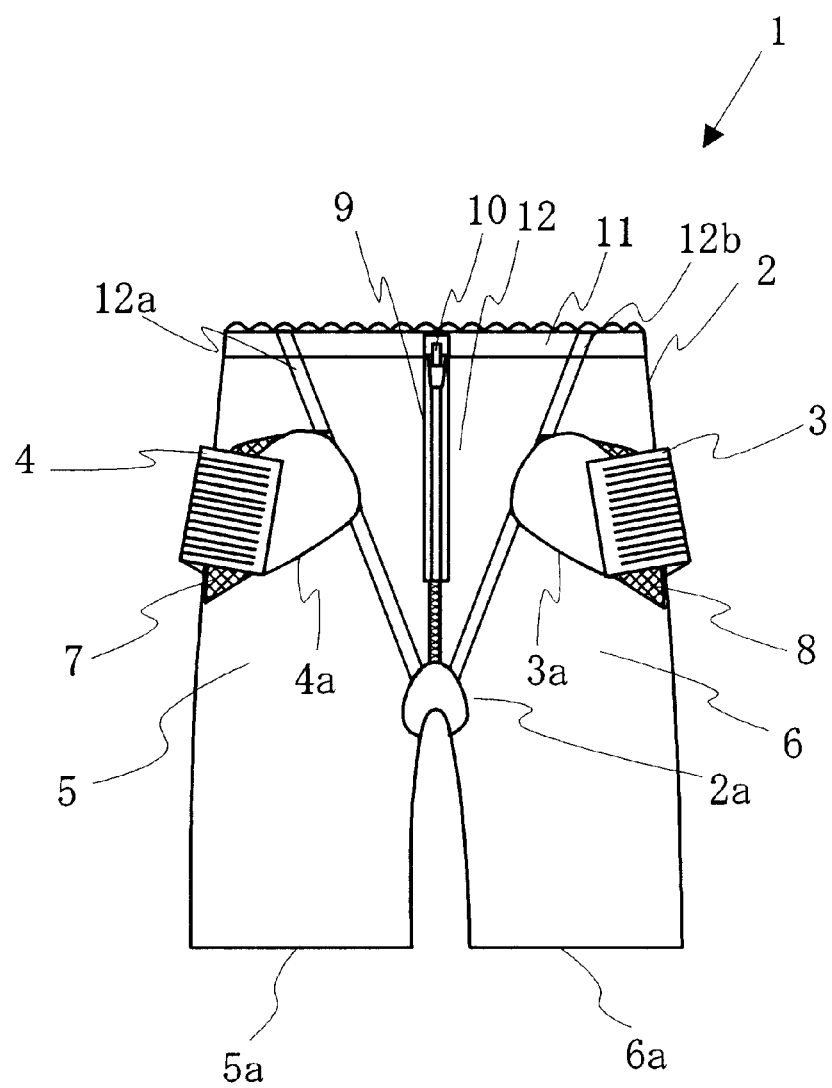
FIG. 3 is a front view showing the first embodiment of the lumbago treating girdle according to the present invention after the stretch band is wound therearound.
Figure 4:
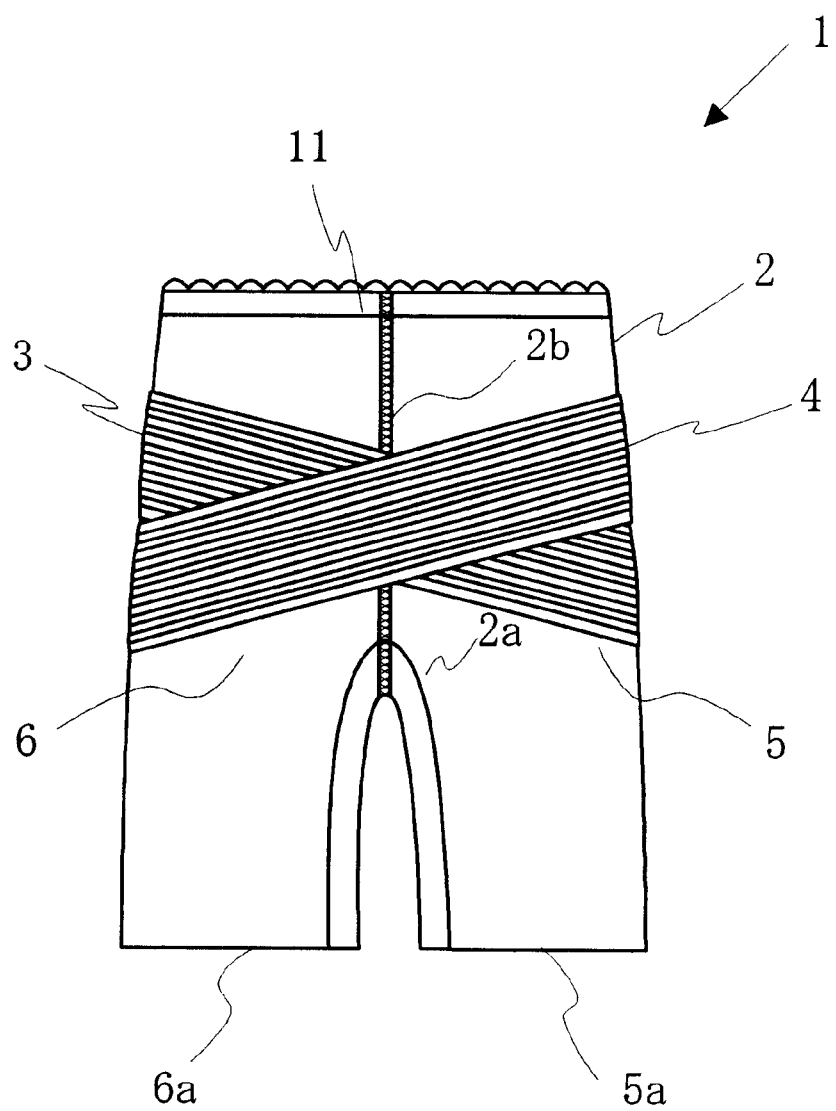
FIG. 4 is a back view showing the first embodiment of the lumbago treating girdle according to the present invention after the stretch band is wound therearound.
Figure 5:
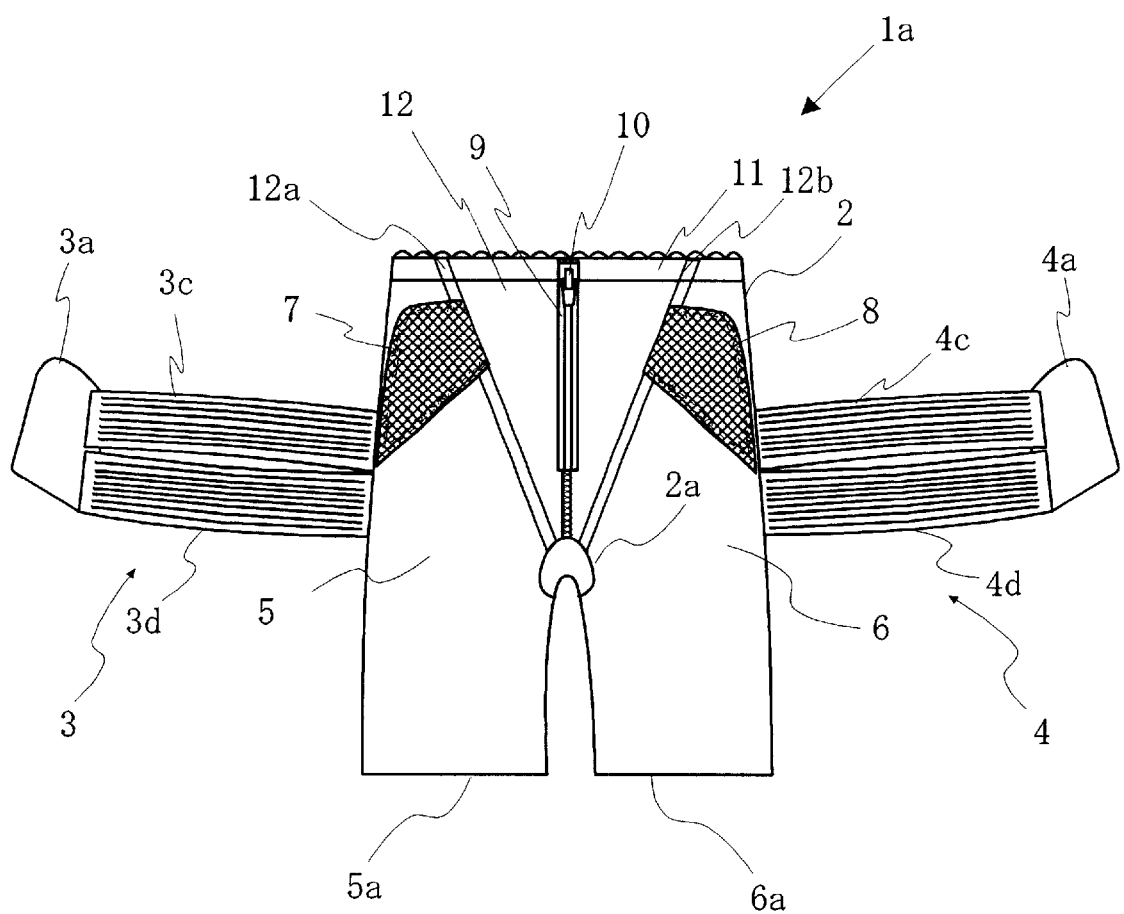
FIG. 5 is a front view showing the second embodiment of the lumbago treating girdle according to the present invention before the stretch band is wound therearound.
Figure 6:
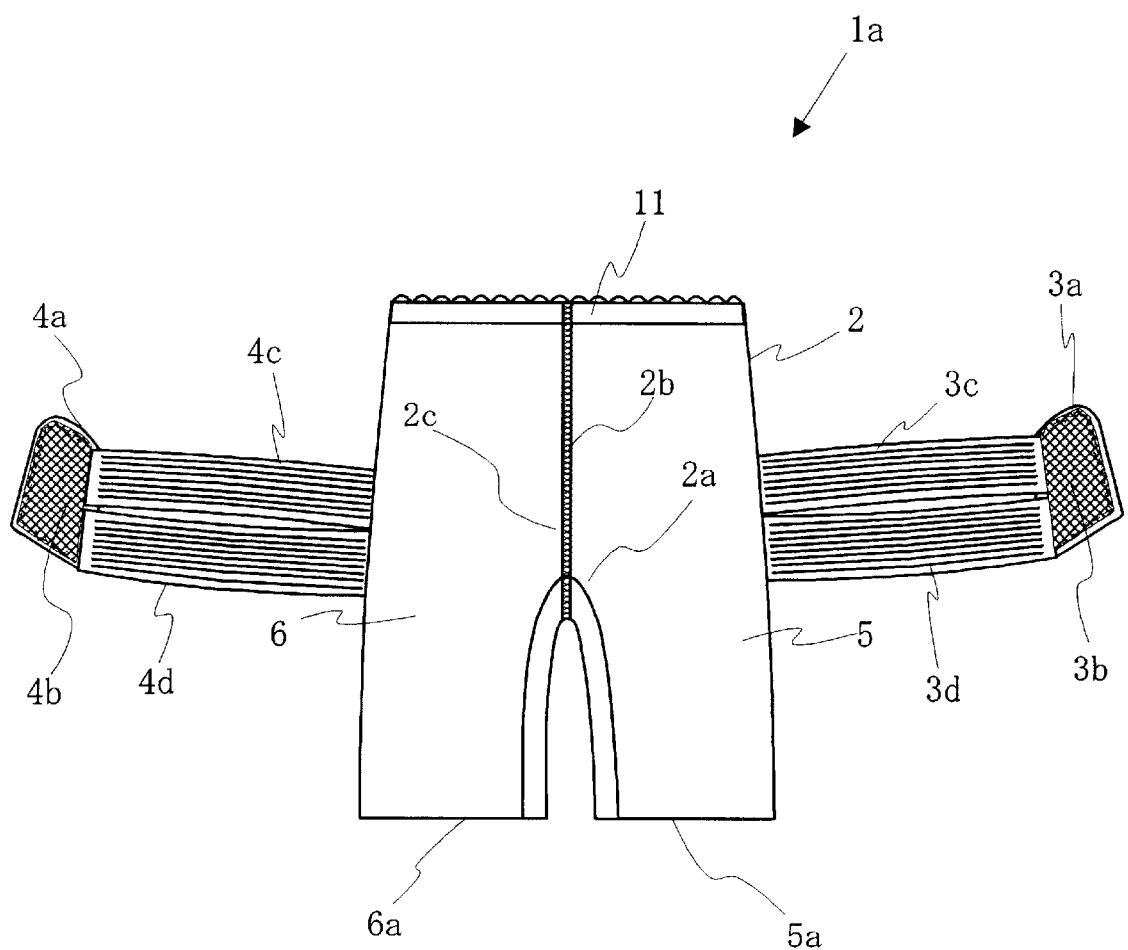
FIG. 6 is a back view showing the second embodiment of the lumbago treating girdle according to the present invention before the stretch band is wound therearound.
Figure 7:
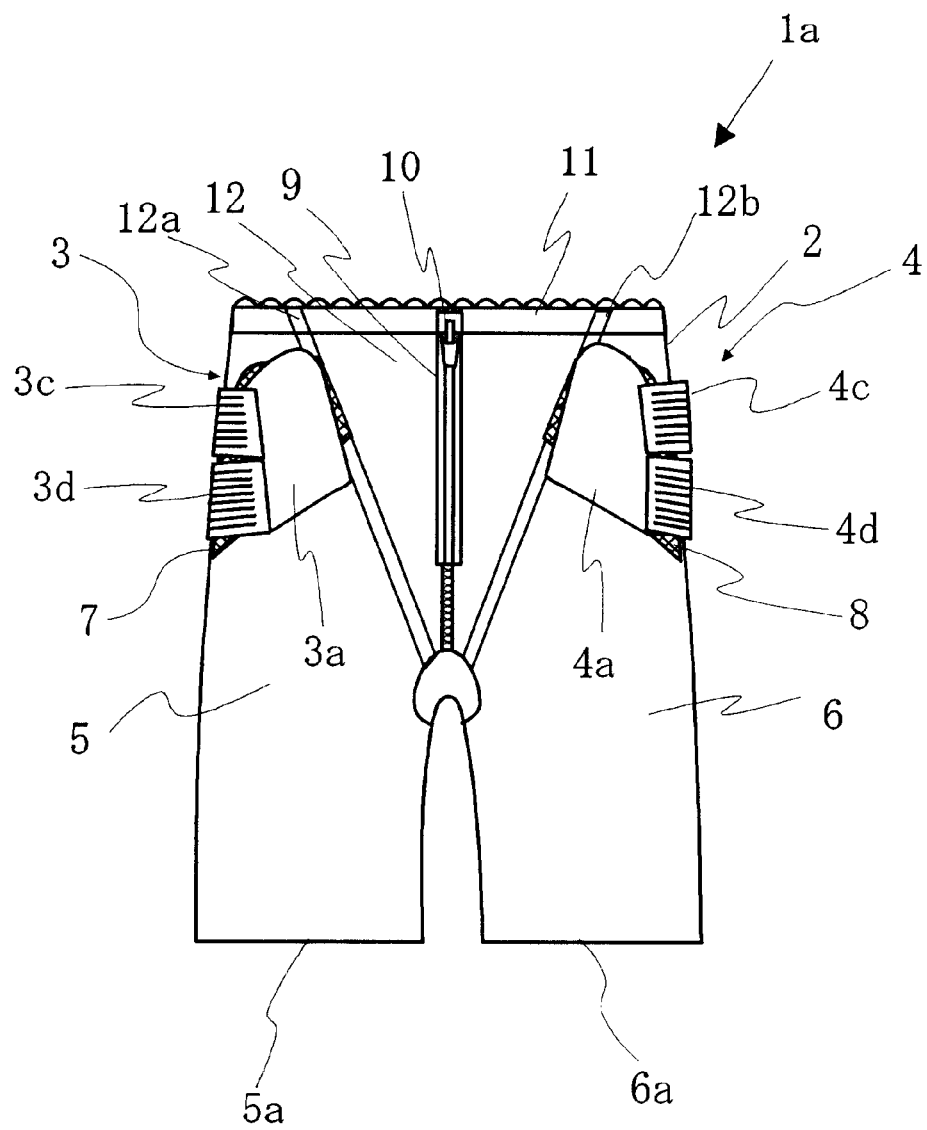
FIG. 7 is a front view showing the second embodiment of the lumbago treating girdle according to the present invention after the stretch band is wound therearound.
Figure 8:
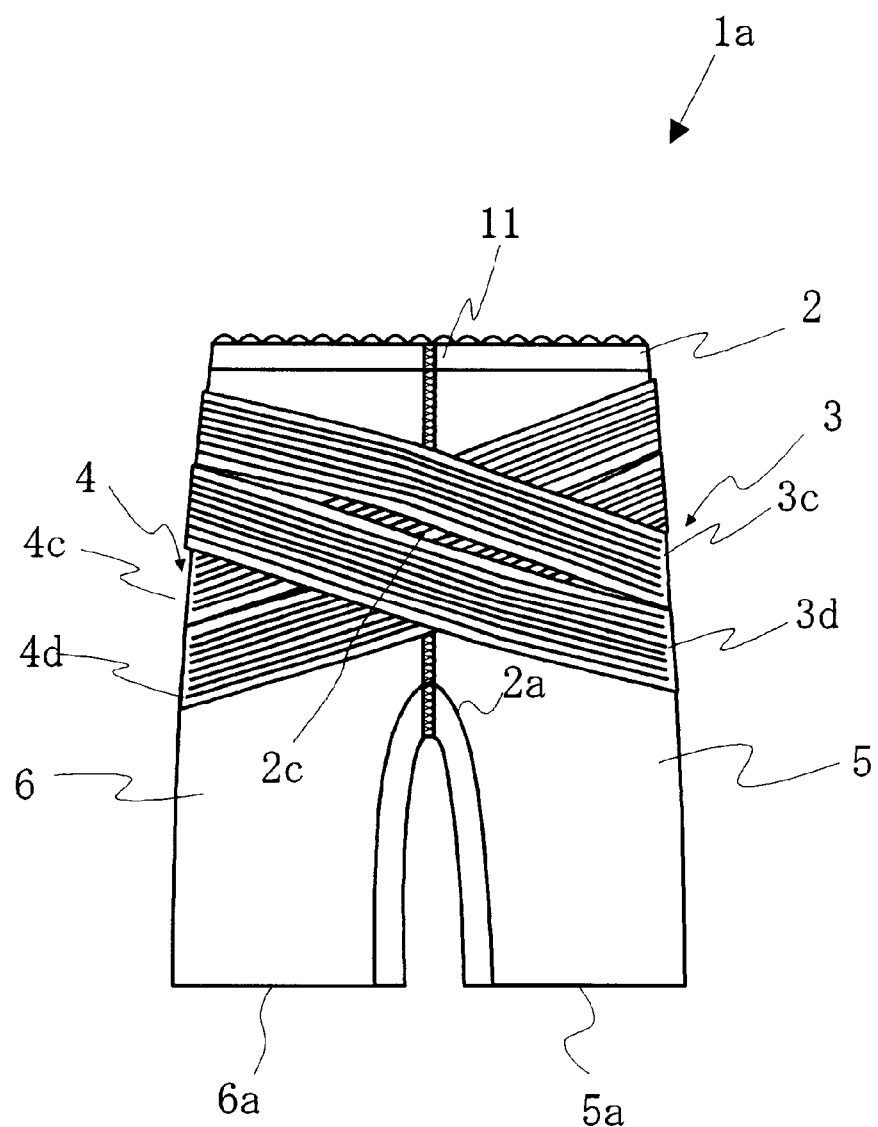
FIG. 8 is a back view showing the second embodiment of the lumbago treating girdle according to the present invention after the stretch band is wound therearound.
Figure 9:
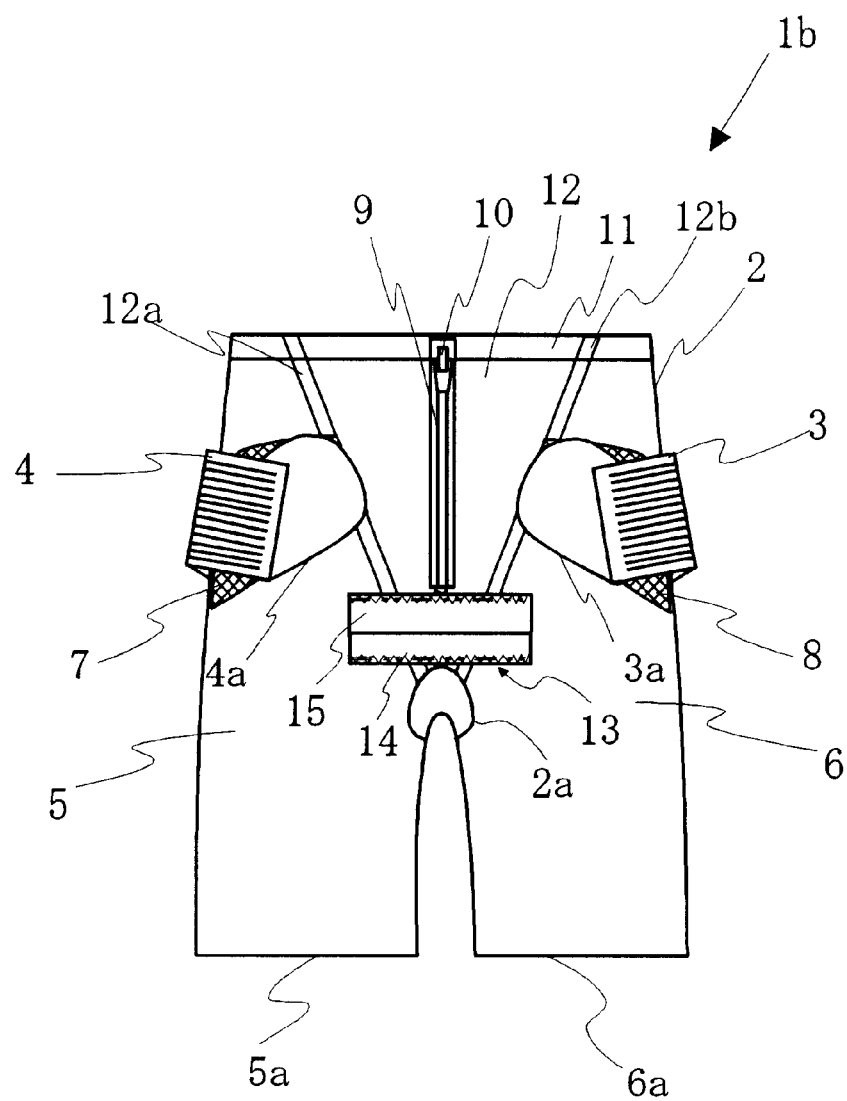
FIG. 9 is a front view showing the third embodiment of the lumbago treating girdle according to the present invention after the stretch band is wound therearound.
Figure 10:
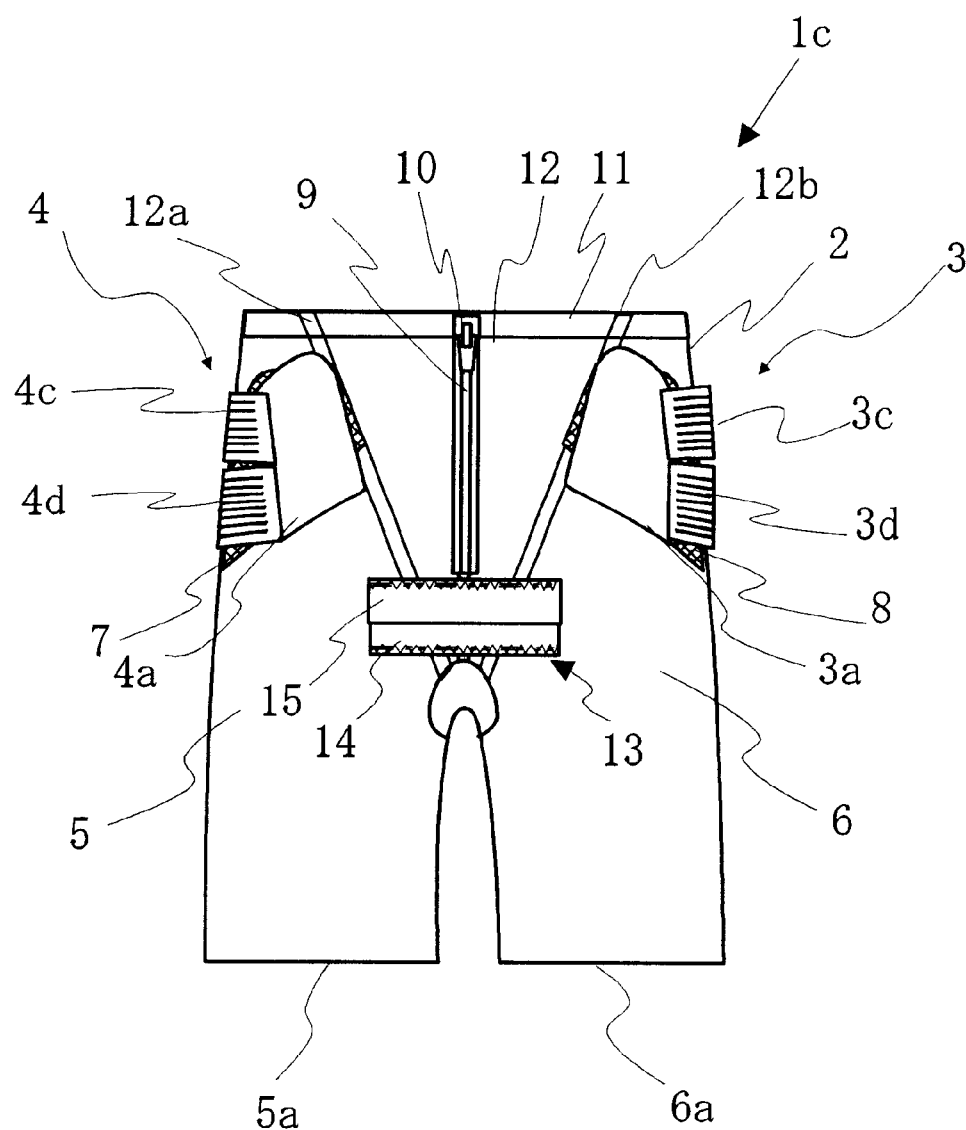
FIG. 10 is a front view showing the fourth embodiment of the lumbago treating girdle according to the present invention after the stretch band is wound therearound.
Figure 11:
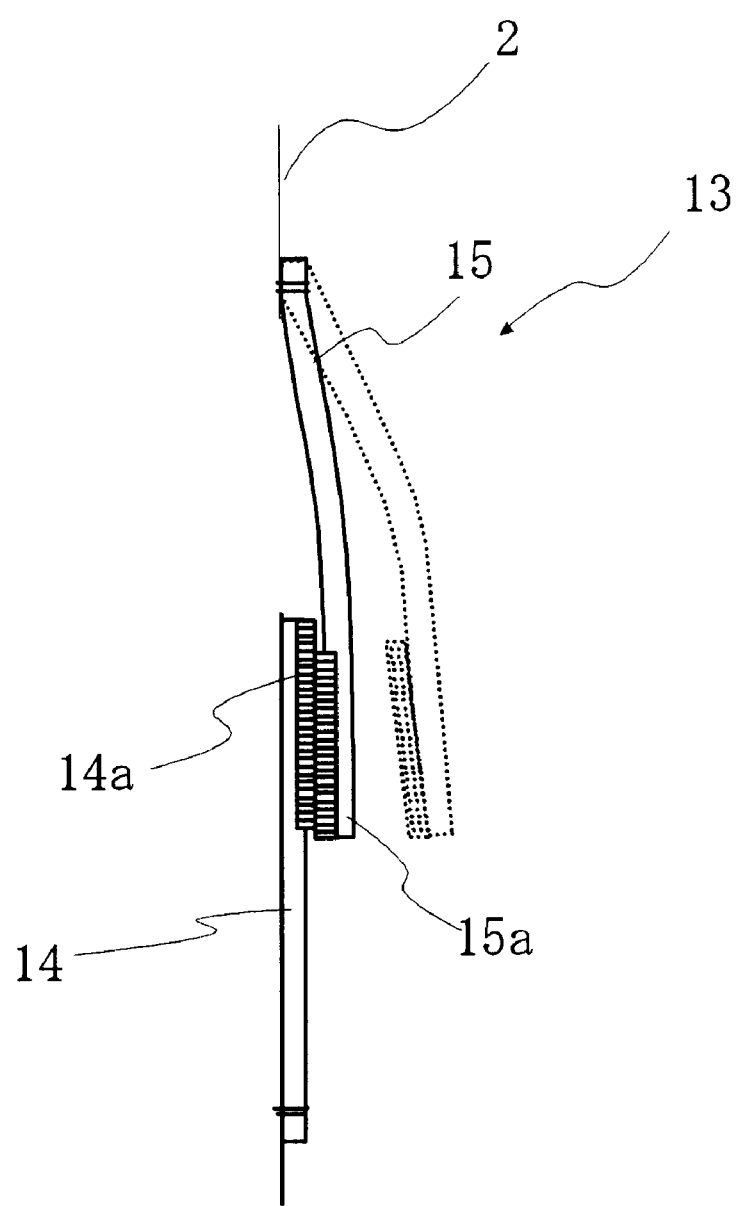
FIG. 11 is a longitudinal sectional view of an opening/closing portion disposed in the third and fourth embodiments of the lumbago treating girdle according to the present invention.
Figure 12:
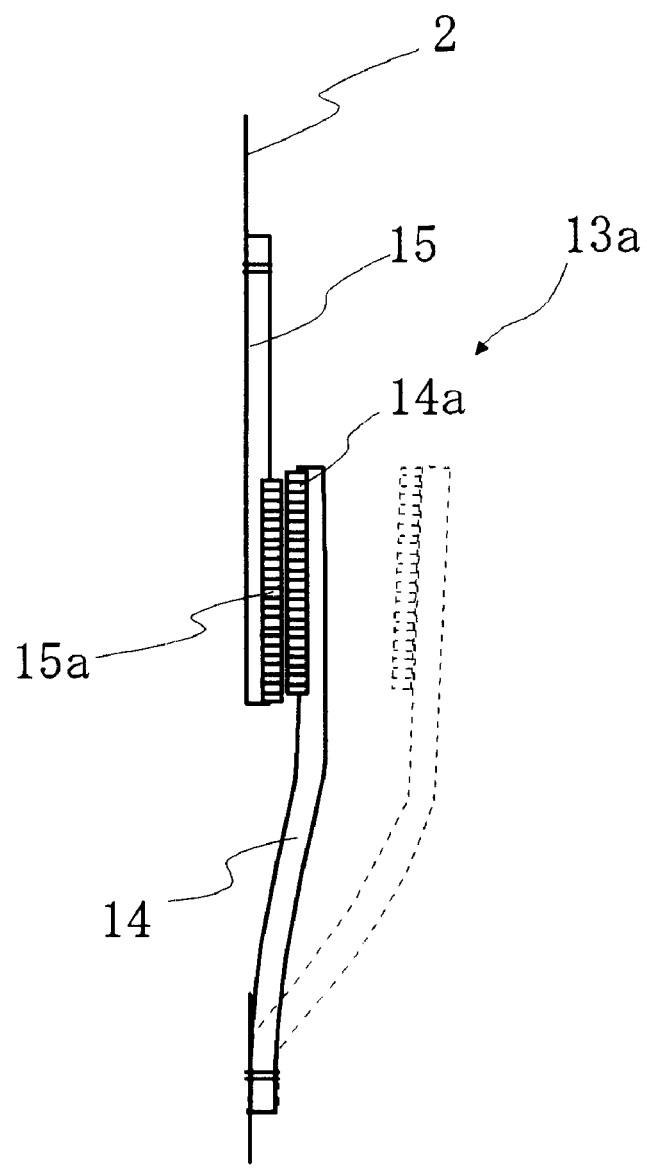
FIG. 12 is a longitudinal sectional view of another example of the opening/closing portion disposed in the third and fourth embodiments of the lumbago treating girdle according to the present invention.
Figure 13:
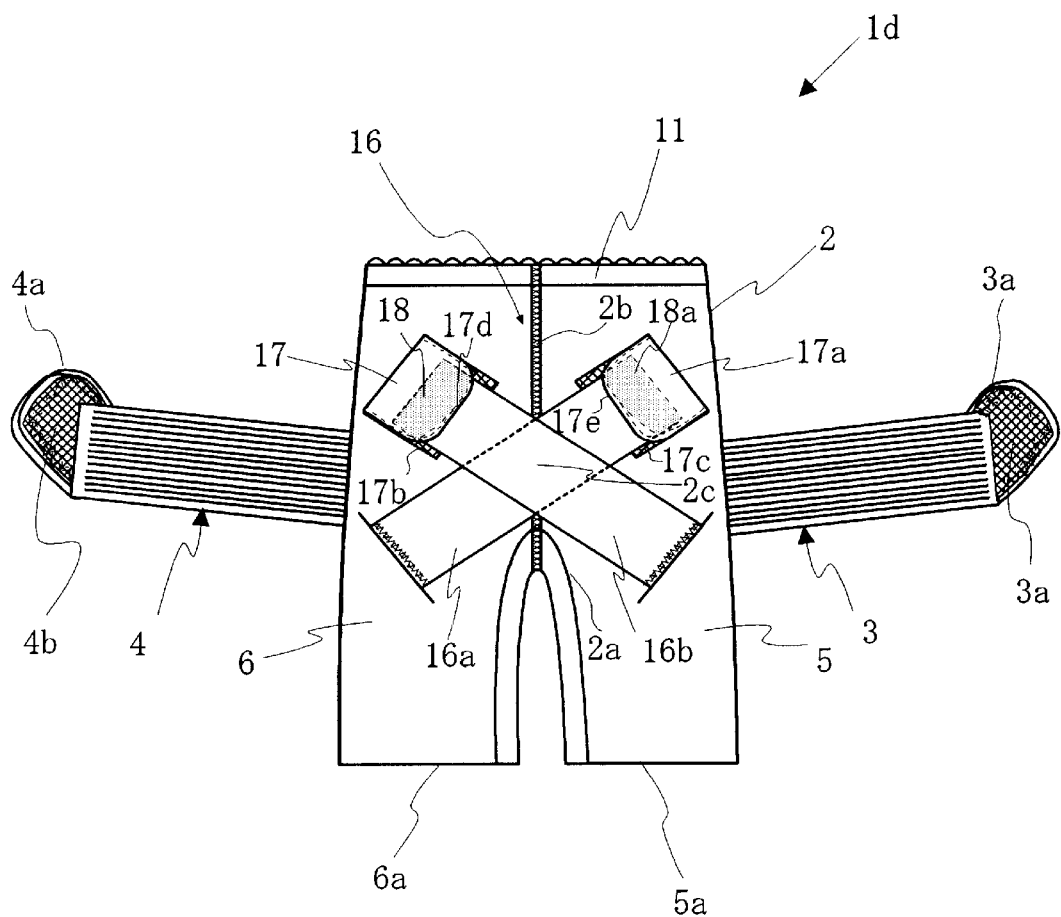
FIG. 13 is a back view showing the fifth embodiment of the lumbago treating girdle according to the present invention before the stretch band is wound therearound.
Figure 14:
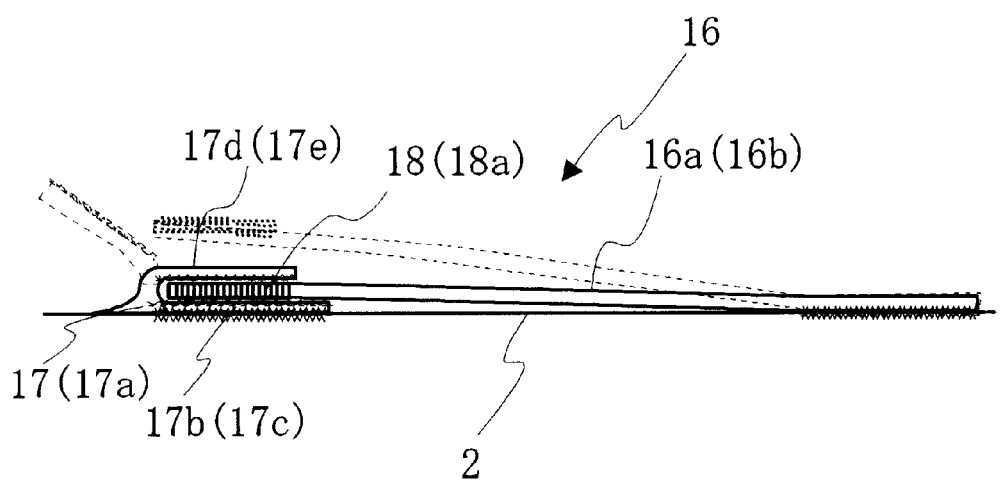
FIG. 14 is a longitudinal sectional view of a cross band of the fifth embodiment of the lumbago treating girdle according to the present invention.
Figure 15:
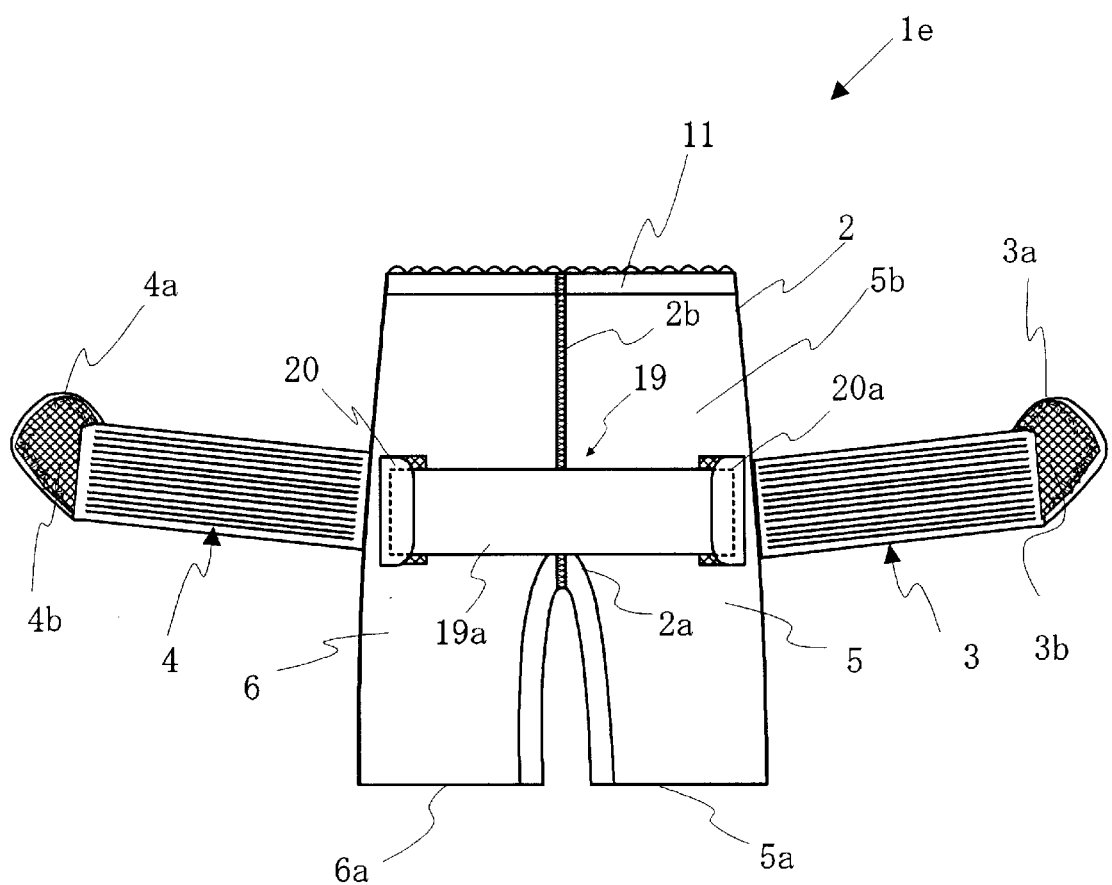
FIG. 15 is a back view showing the sixth embodiment of the lumbago treating girdle according to the present invention before the stretch band is wound therearound.
Figure 16:
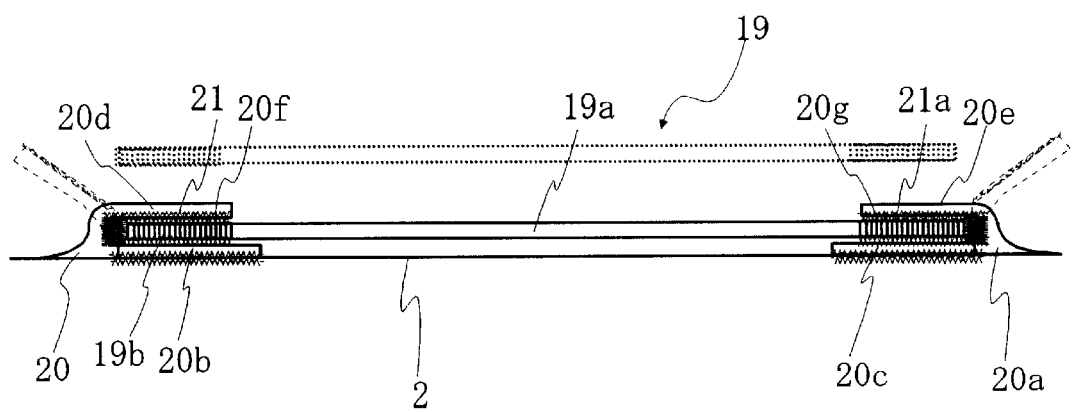
FIG. 16 is a longitudinal sectional view of a horizontal band of the sixth embodiment of the lumbago treating girdle according to the present invention.
Figure 17:
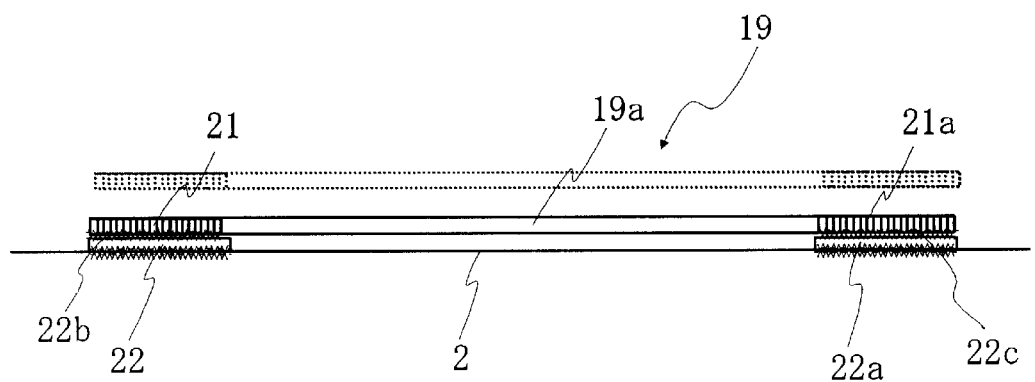
FIG. 17 is a longitudinal sectional view of another example of the horizontal band disposed in the sixth embodiment of the lumbago treating girdle according to the present invention.
Figure 18:
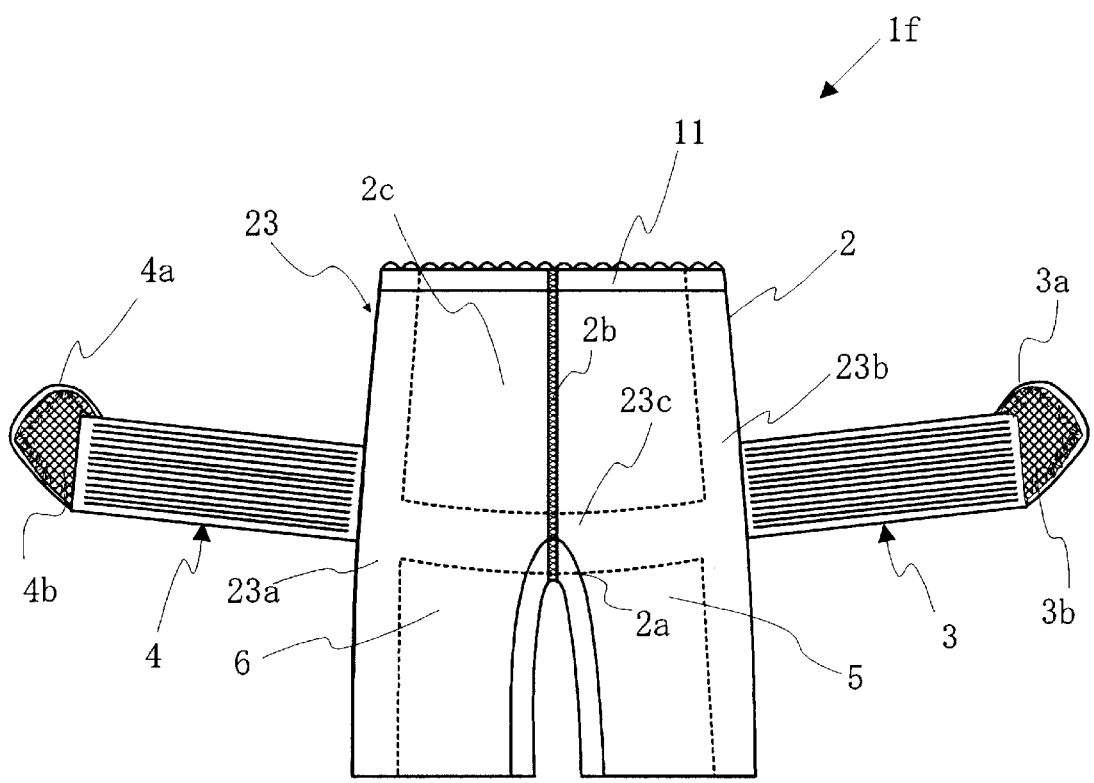
FIG. 18 is a back view showing the seventh embodiment of the lumbago treating girdle according to the present invention before the stretch band is wound therearound.
Figure 19:
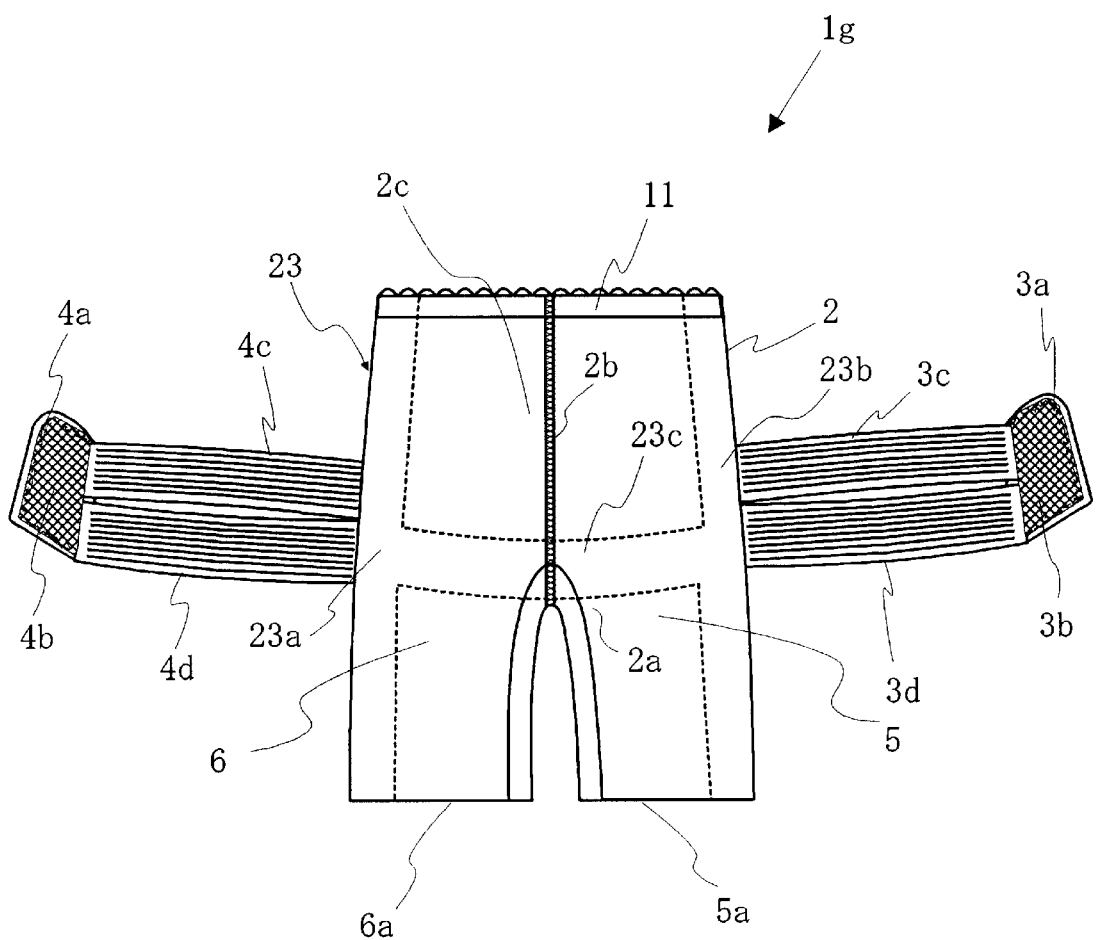
FIG. 19 is a back view showing the eighth embodiment of the lumbago treating girdle according to the present invention before the stretch band is wound therearound.
Figure 20:
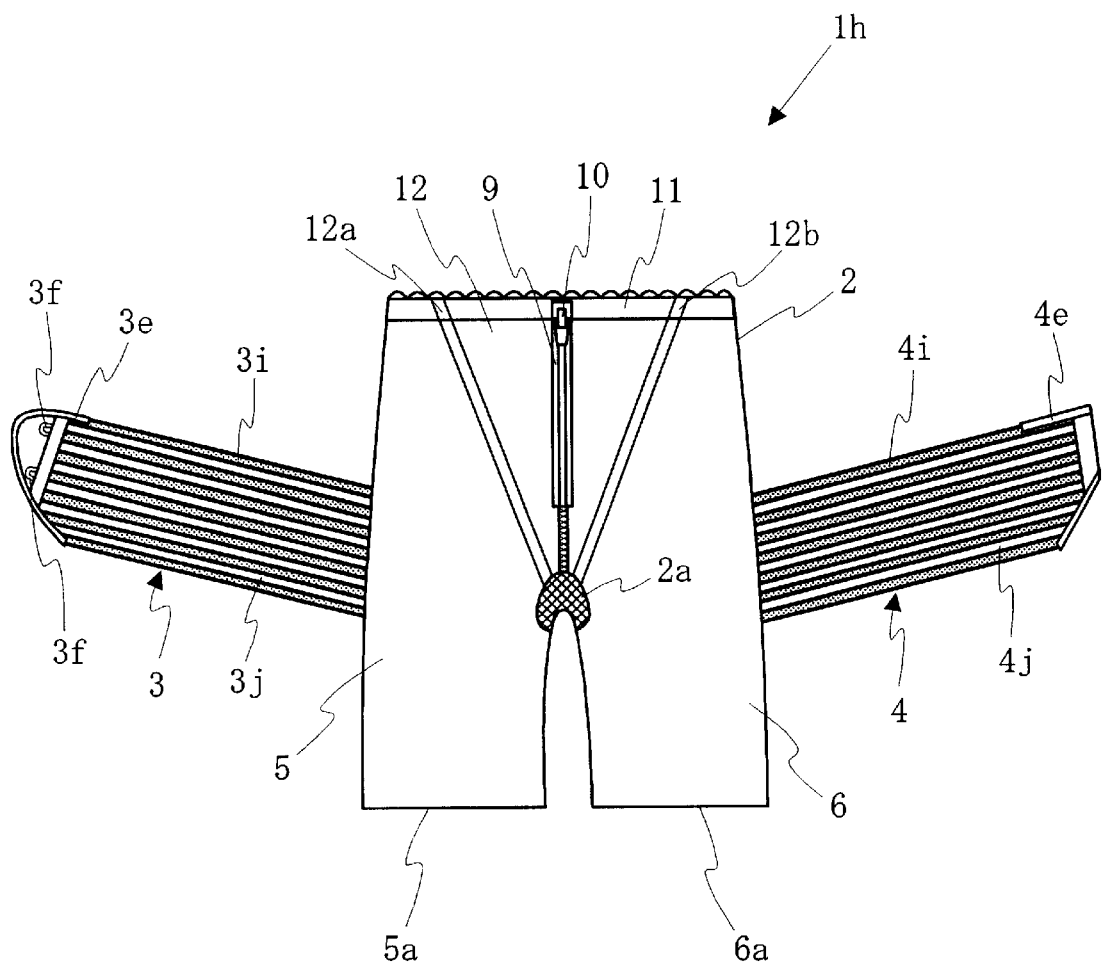
FIG. 20 is a front view showing the ninth embodiment of the lumbago treating girdle according to the present invention before the stretch band is wound therearound.
Figure 21:
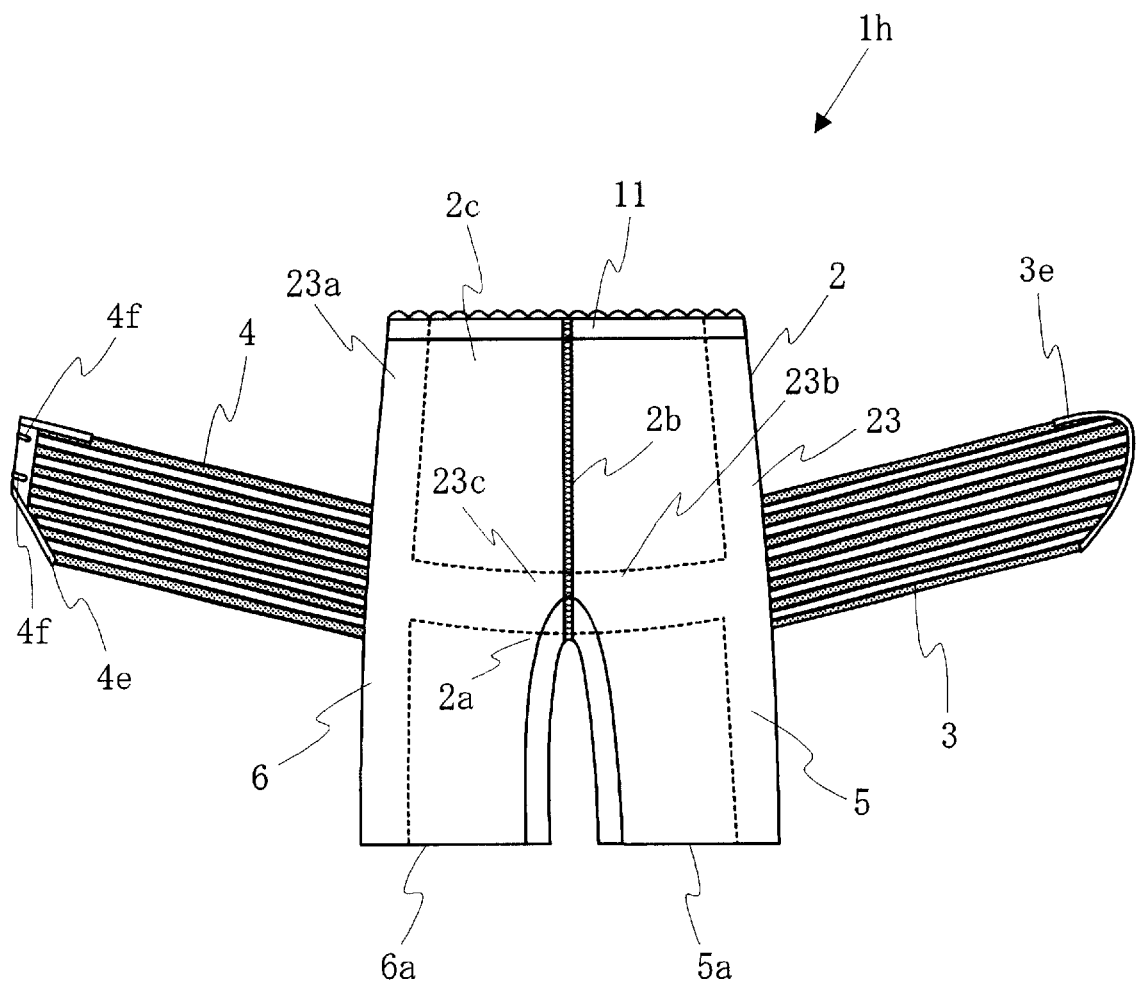
FIG. 21 is a back view showing the ninth embodiment of the lumbago treating girdle according to the present invention before the stretch band is wound therearound.
Figure 22:
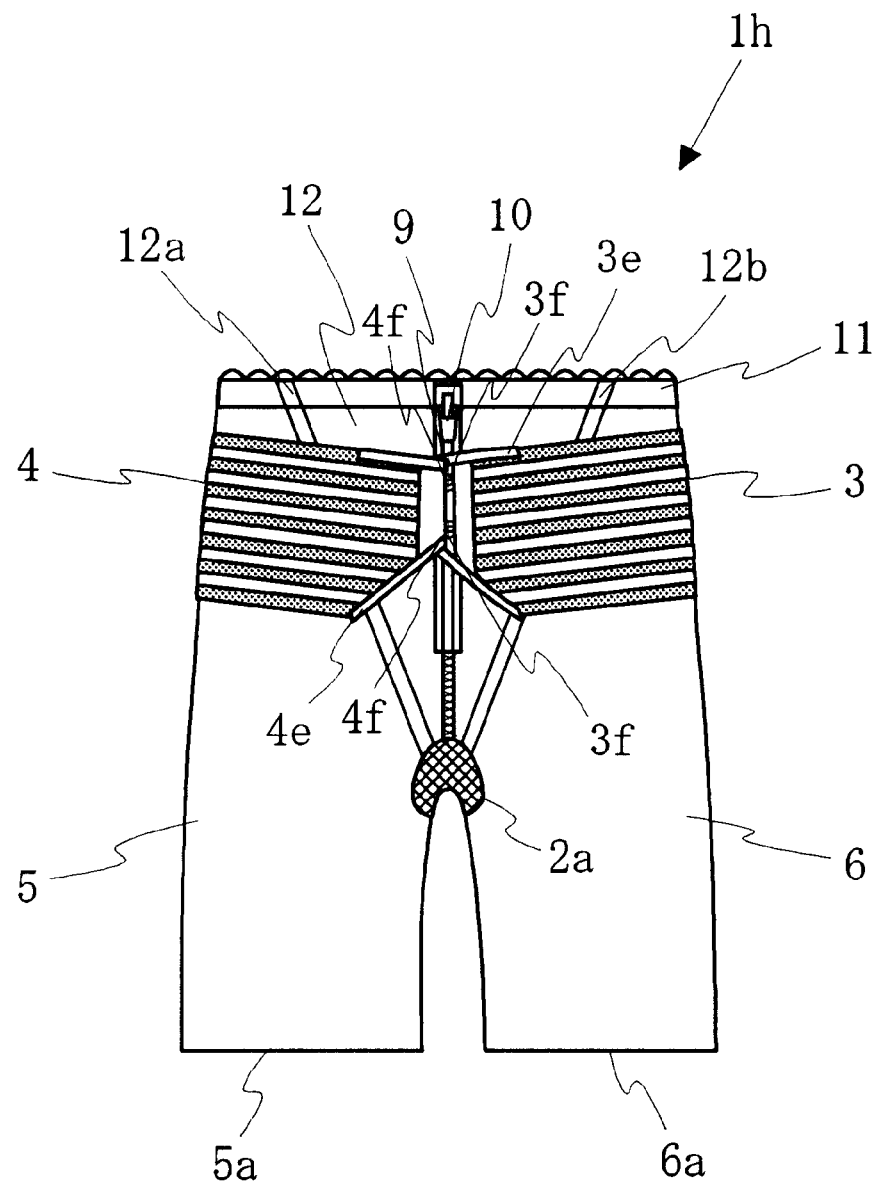
FIG. 22 is a front view showing the ninth embodiment of the lumbago treating girdle according to the present invention after the stretch band was wound therearound.
Figure 23:
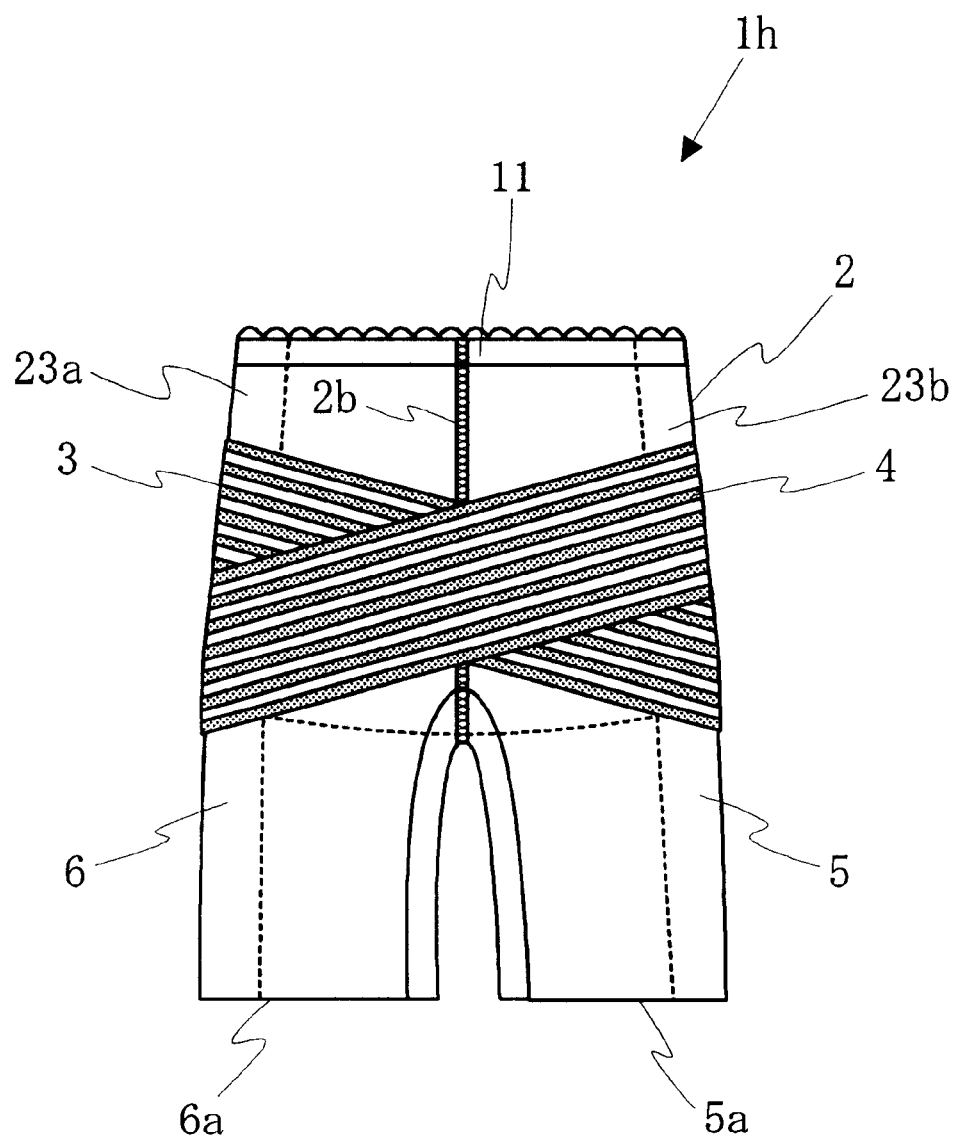
FIG. 23 is a back view showing the ninth embodiment of the lumbago treating girdle according to the present invention after the stretch band was wound therearound.
Figure 24:
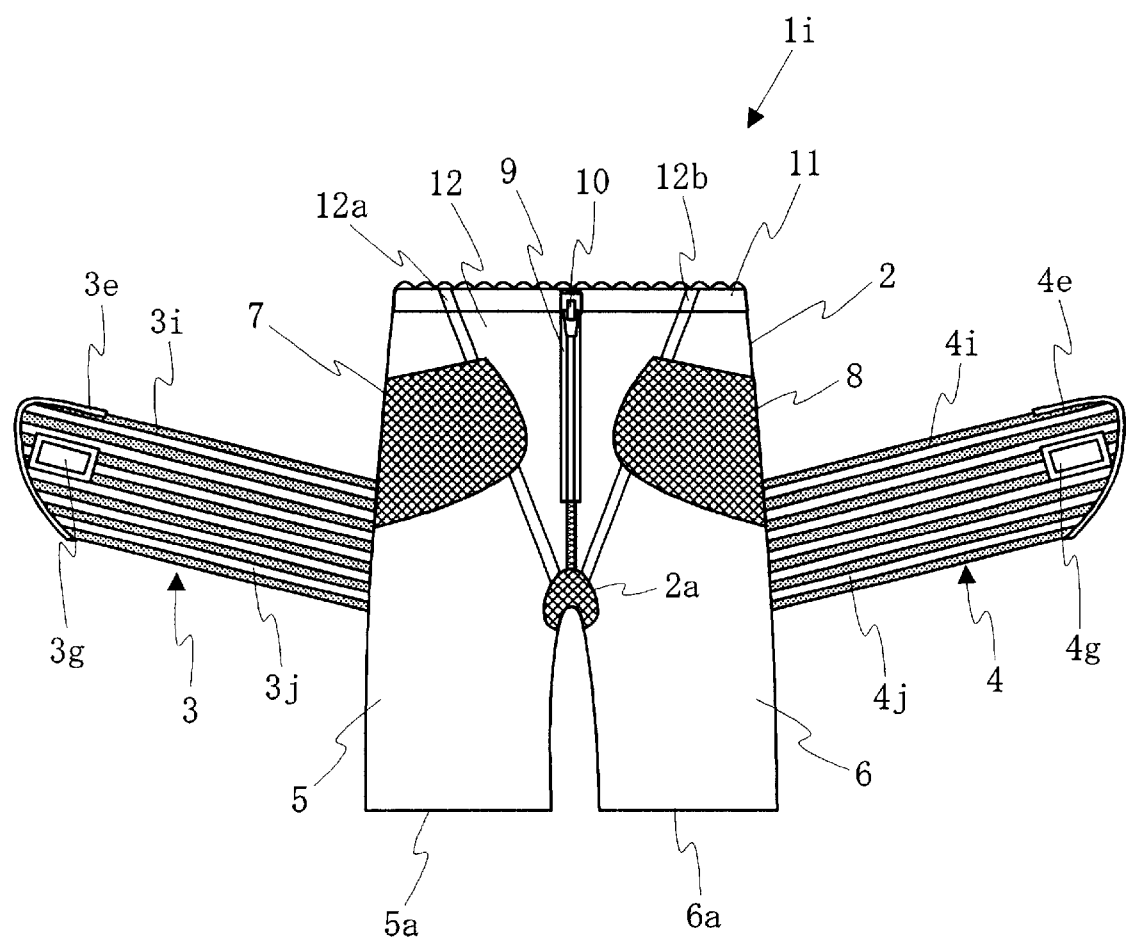
FIG. 24 is a front view showing the tenth embodiment of the lumbago treating girdle according to the present invention before the stretch band is wound therearound.
Figure 25:
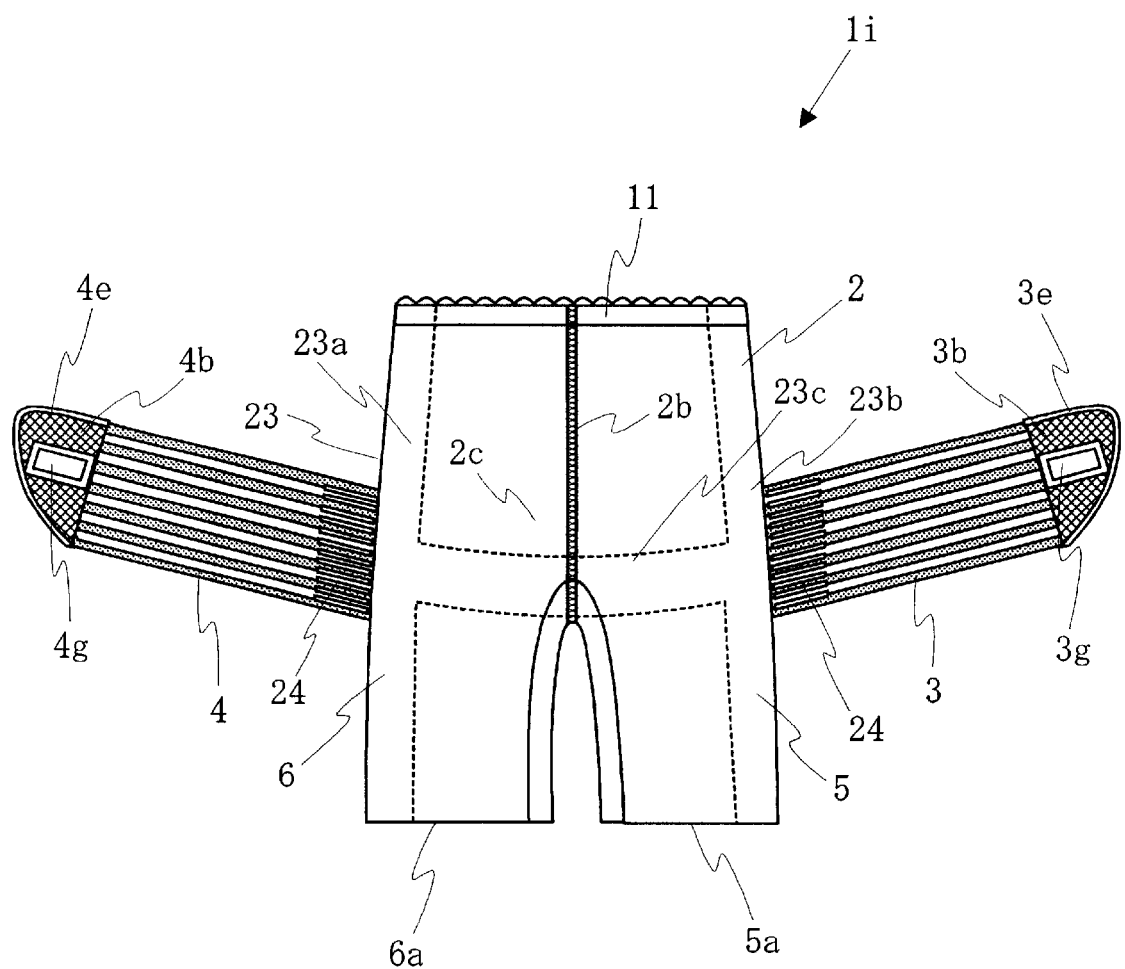
FIG. 25 is a back view showing the tenth embodiment of the lumbago treating girdle according to the present invention before the stretch band is wound therearound.
Figure 26:
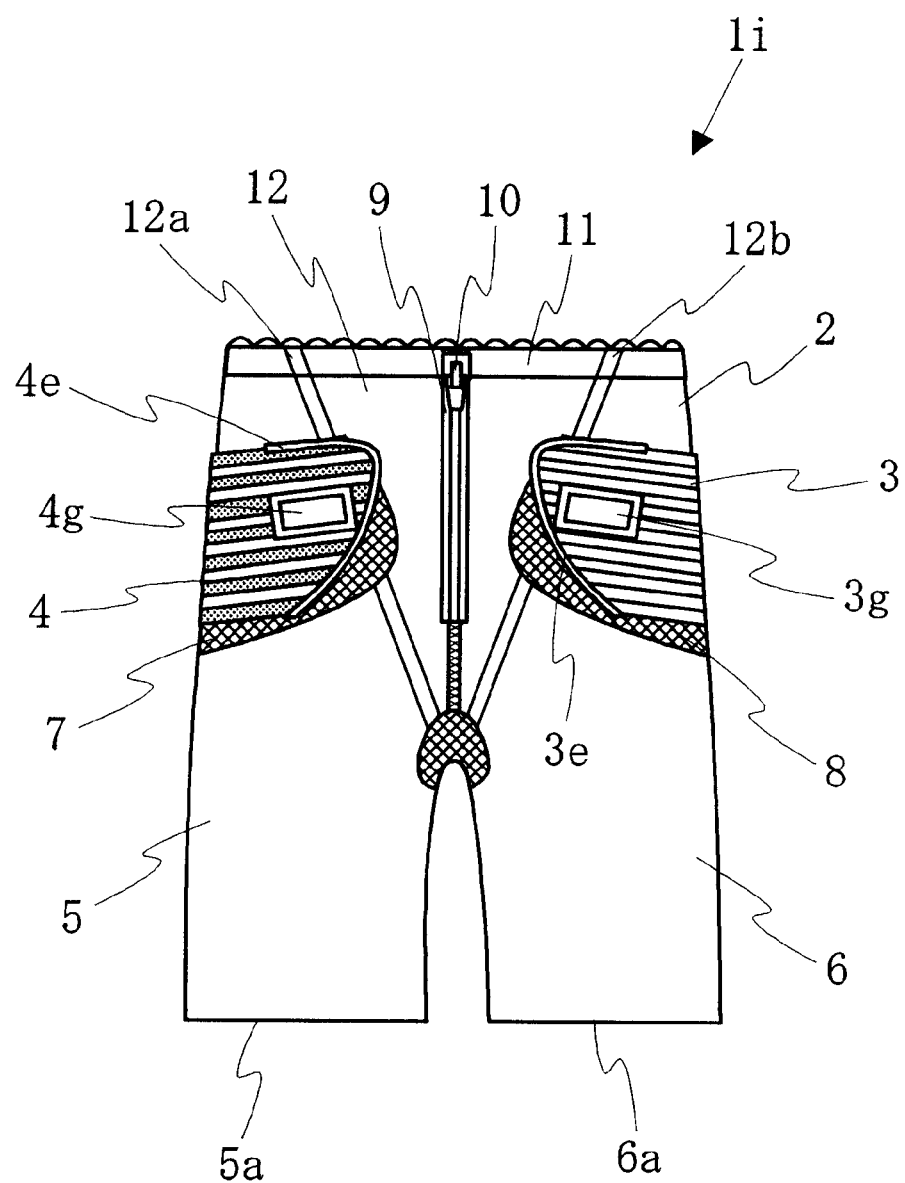
FIG. 26 is a front view showing the tenth embodiment of the lumbago treating girdle according to the present invention after the stretch band was wound therearound.
Figure 27:
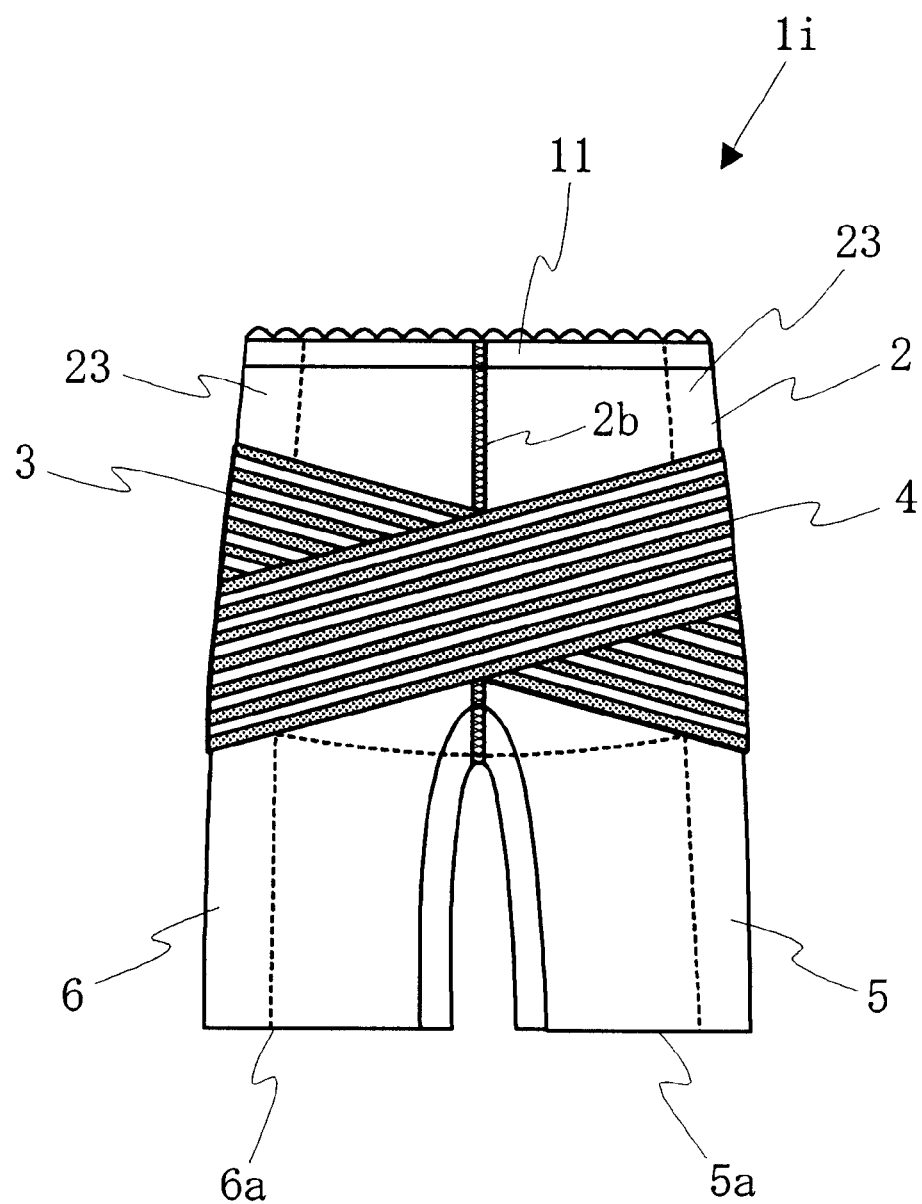
FIG. 27 is a back view showing the tenth embodiment of the lumbago treating girdle according to the present invention after the stretch band was wound therearound.
Figure 28:
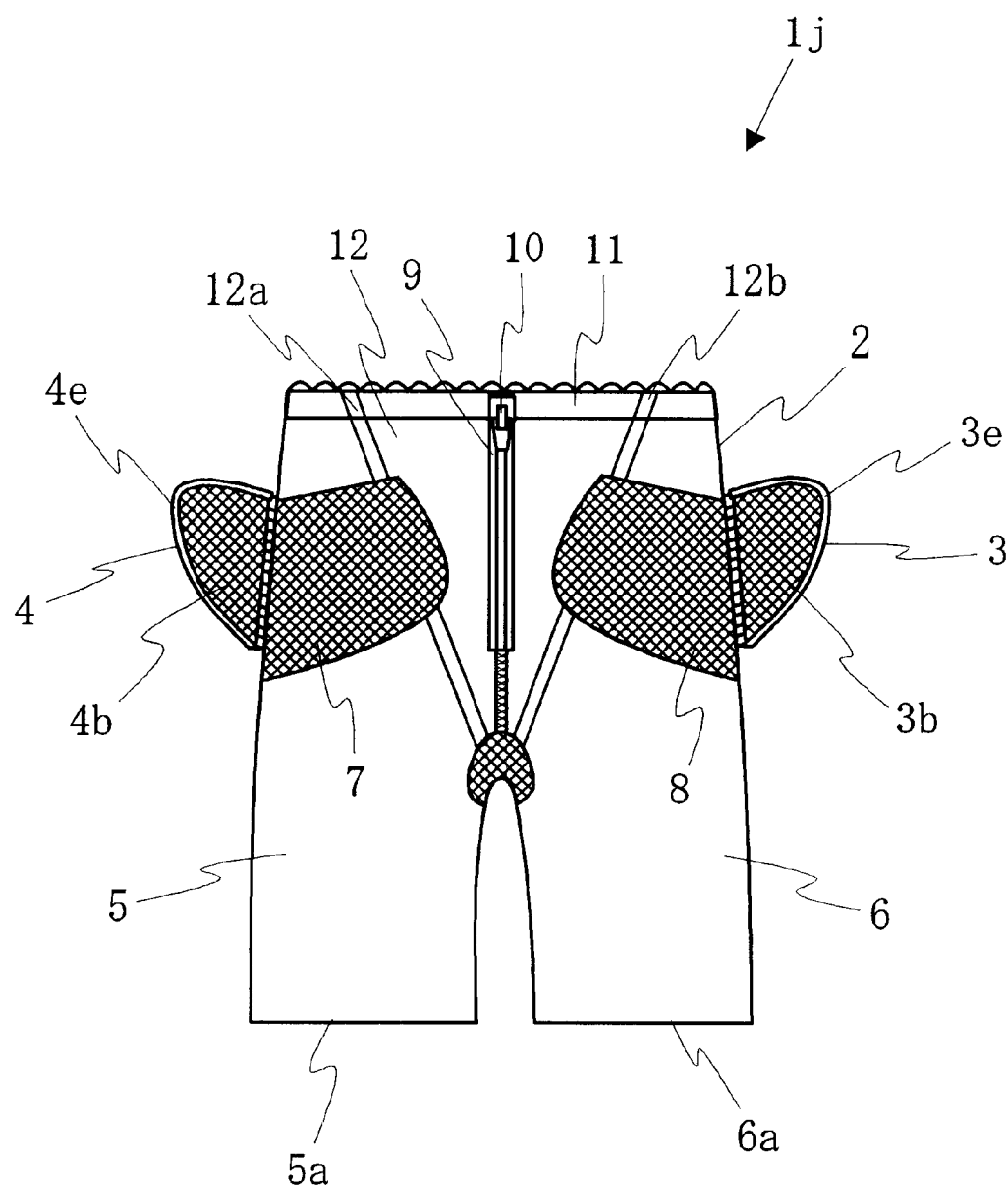
FIG. 28 is a front view showing the eleventh embodiment of the lumbago treating girdle according to the present invention before the stretch band is wound therearound.
Figure 29:
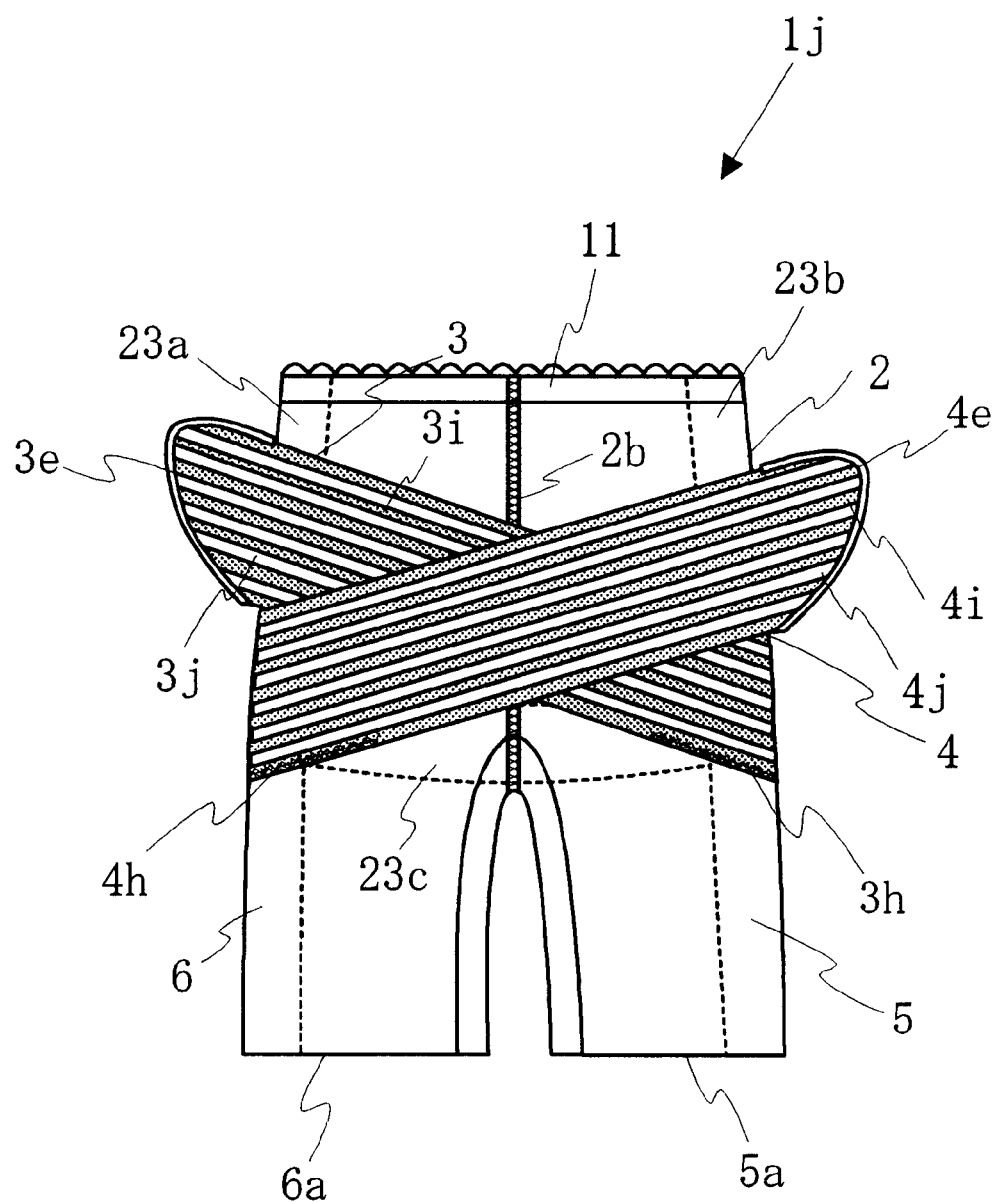
FIG. 29 is a back view showing the eleventh embodiment of the lumbago treating girdle according to the present invention before the stretch band is wound therearound.
Figure 30:
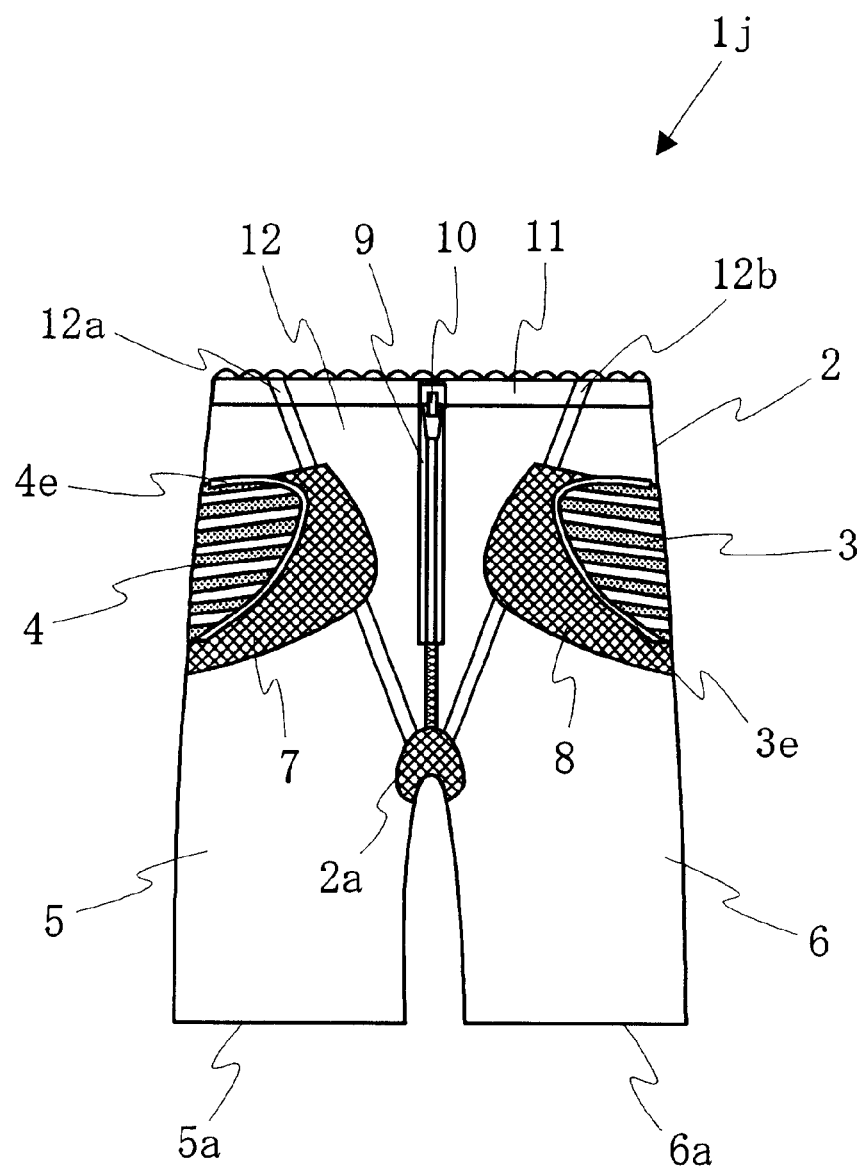
FIG. 30 is a front view showing the eleventh embodiment of the lumbago treating girdle according to the present invention after the stretch band was wound therearound.
Figure 31:
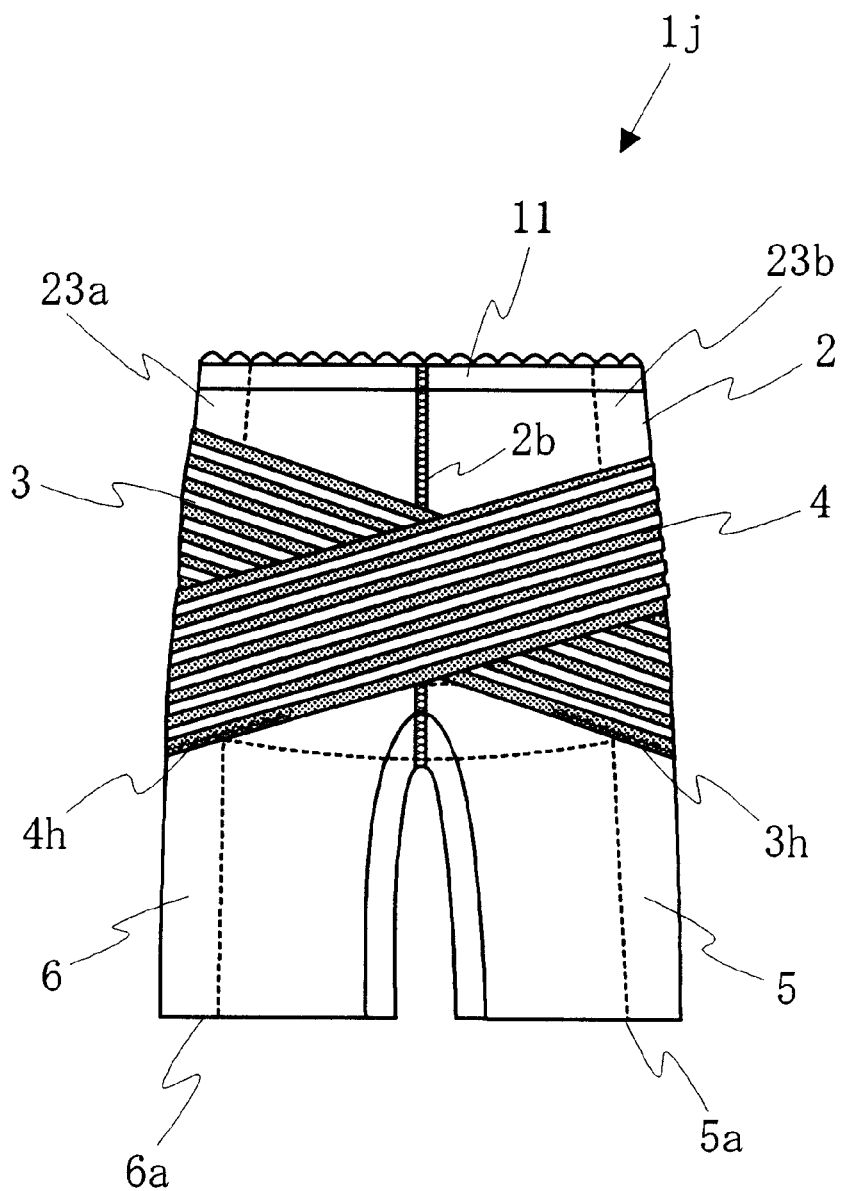
FIG. 31 is a back view showing the eleventh embodiment of the lumbago treating girdle according to the present invention after the stretch band was wound therearound.
Figure 32:
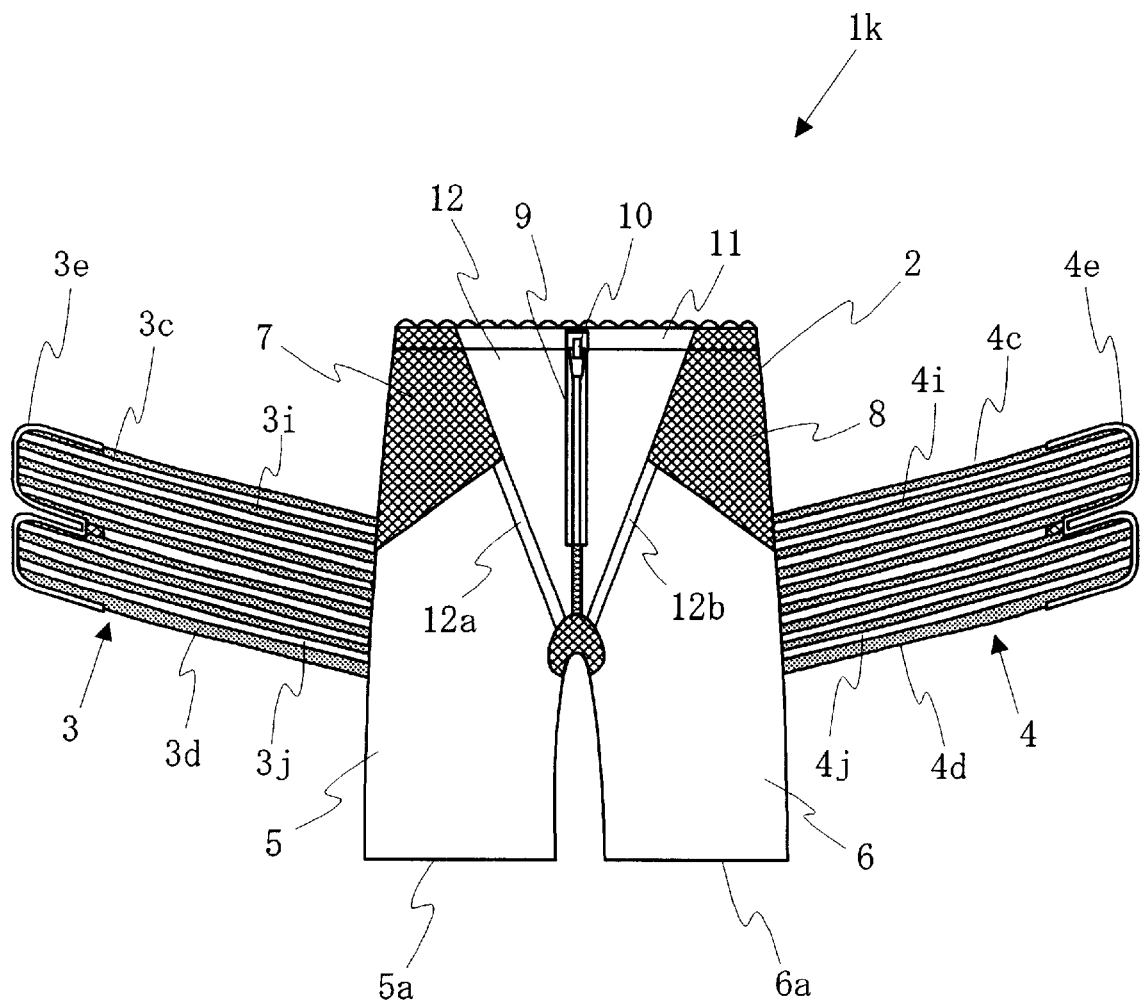
FIG. 32 is a front view showing the twelfth embodiment of the lumbago treating girdle according to the present invention before the stretch band is wound therearound.
Figure 33:
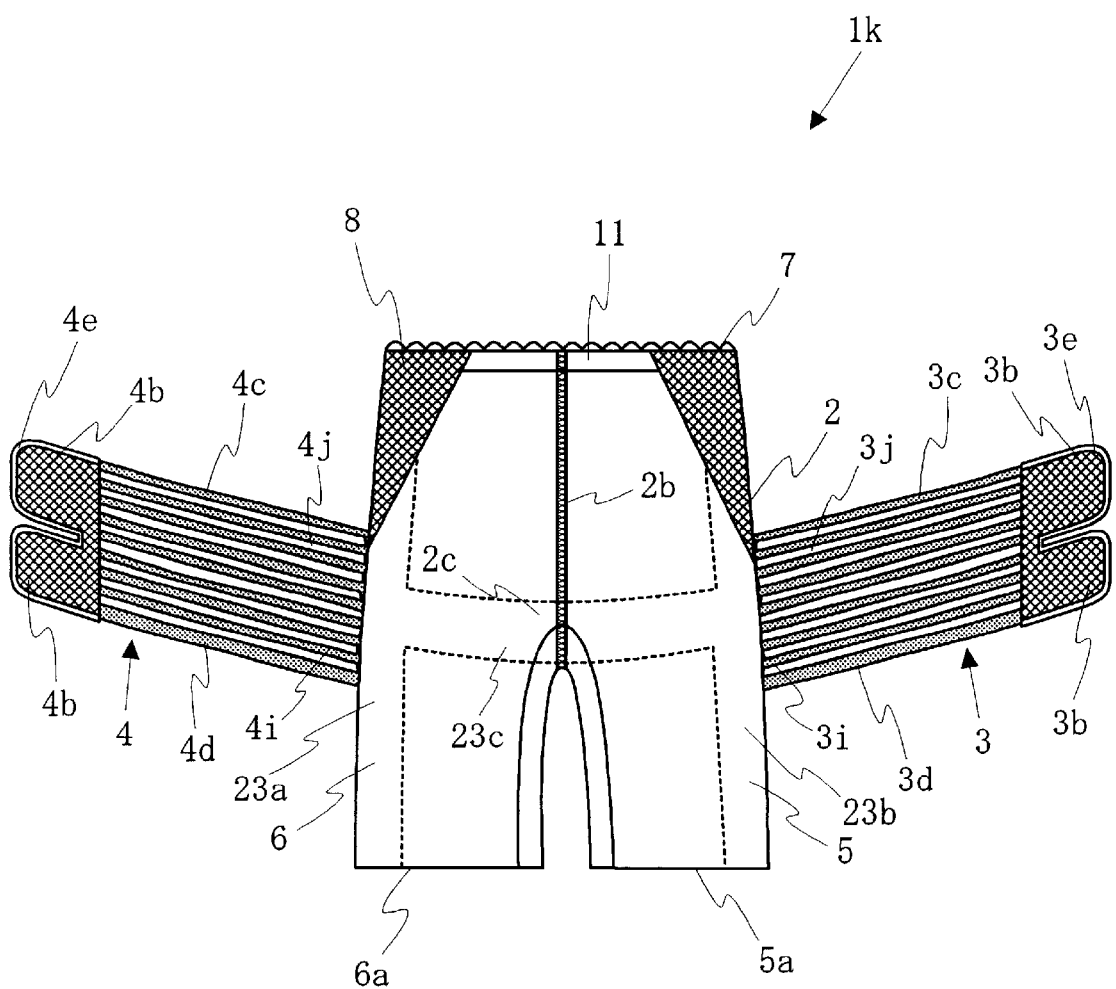
FIG. 33 is a back view showing the twelfth embodiment of the lumbago treating girdle according to the present invention before the stretch band is wound therearound.
Figure 34:
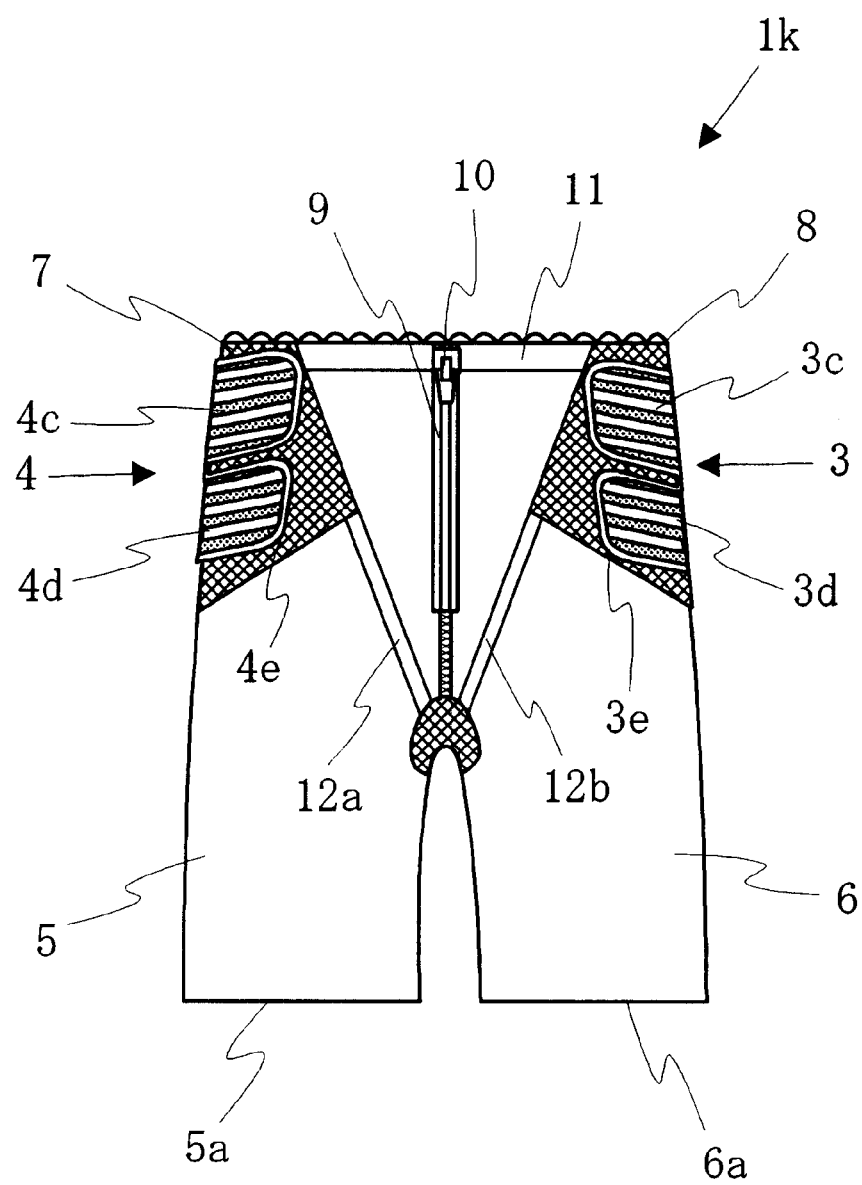
FIG. 34 is a front view showing the twelfth embodiment of the lumbago treating girdle according to the present invention after the stretch band was wound therearound.
Figure 35:
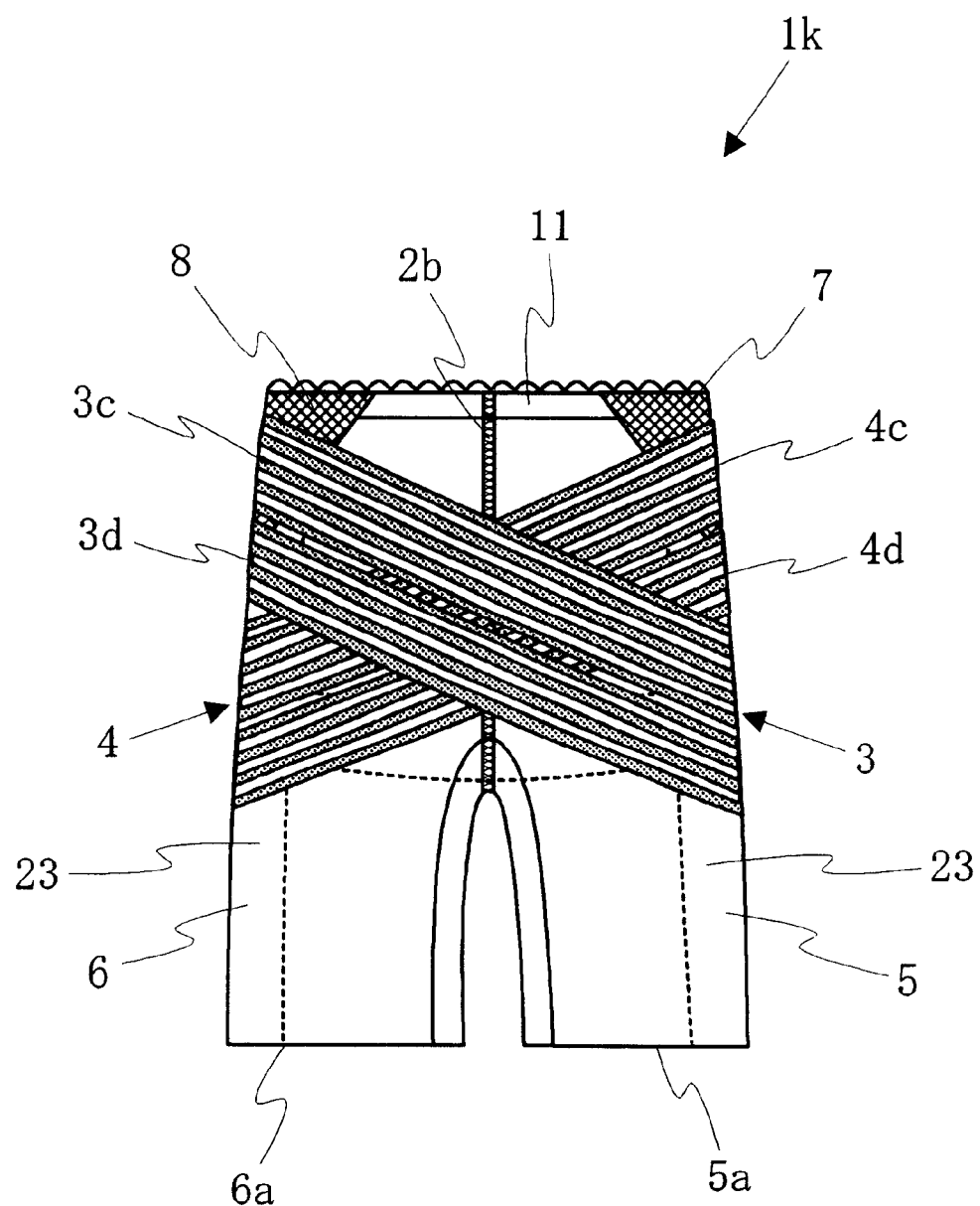
FIG. 35 is a back view showing the twelfth embodiment of the lumbago treating girdle according to the present invention after the stretch band was wound therearound.
Figure 36:
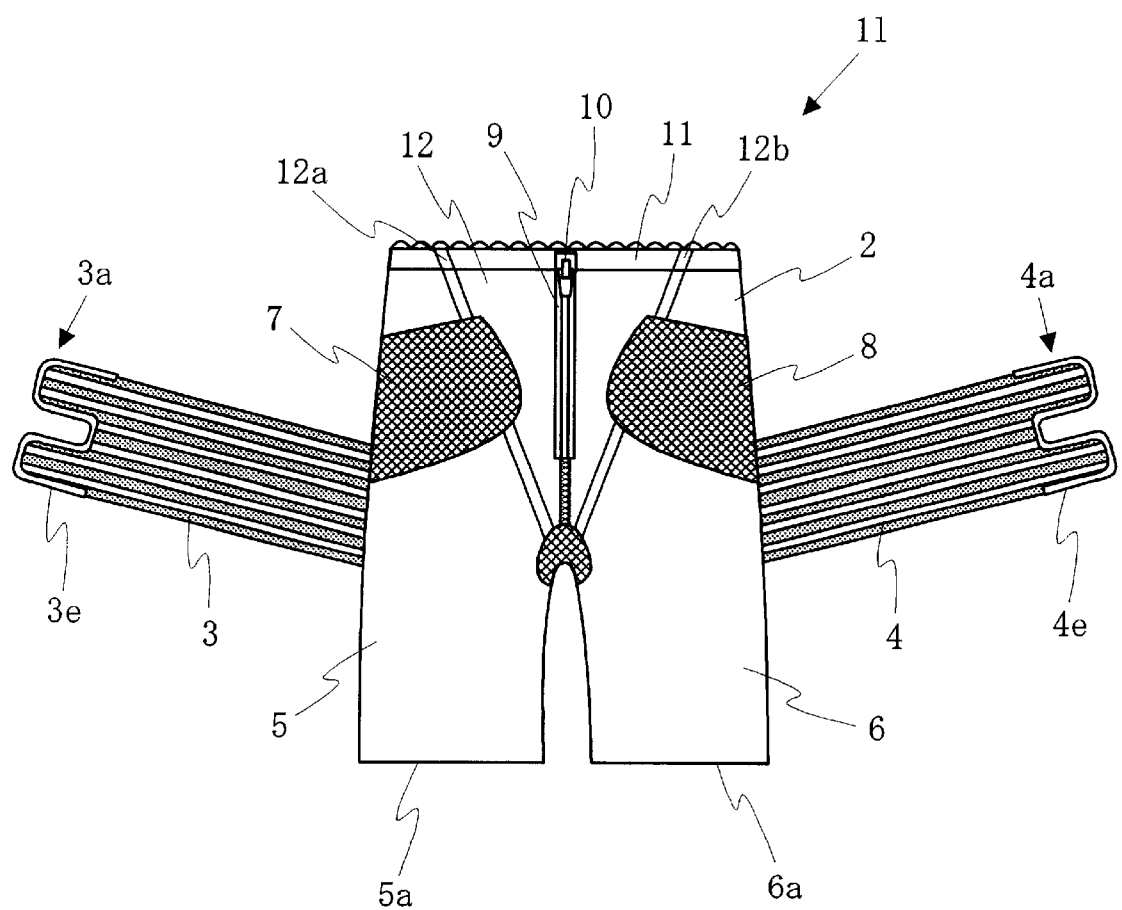
FIG. 36 is a front view showing the thirteenth embodiment of the lumbago treating girdle according to the present invention before the stretch band is wound therearound.
Figure 37:
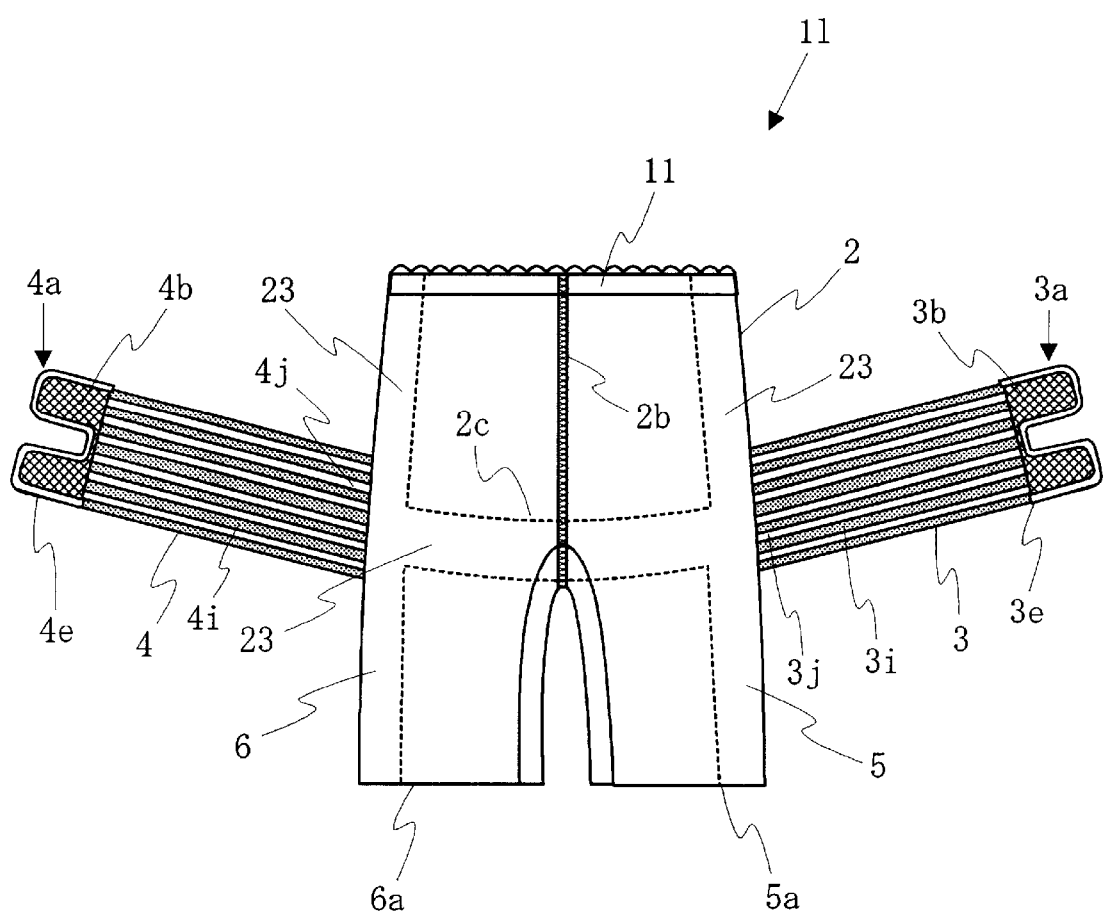
FIG. 37 is a back view showing the thirteenth embodiment of the lumbago treating girdle according to the present invention before the stretch band is wound therearound.
Figure 38:
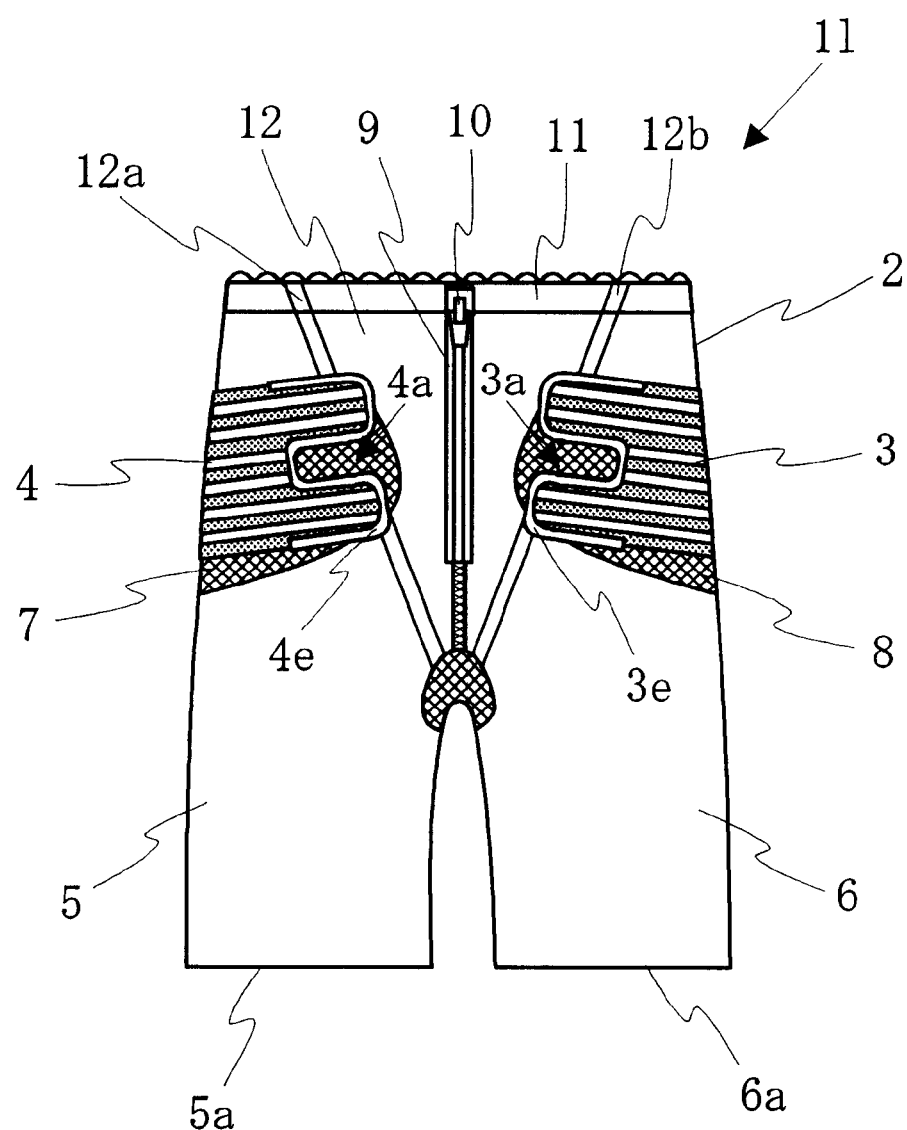
FIG. 38 is a front view showing the thirteenth embodiment of the lumbago treating girdle according to the present invention after the stretch band was wound therearound.
Figure 39:
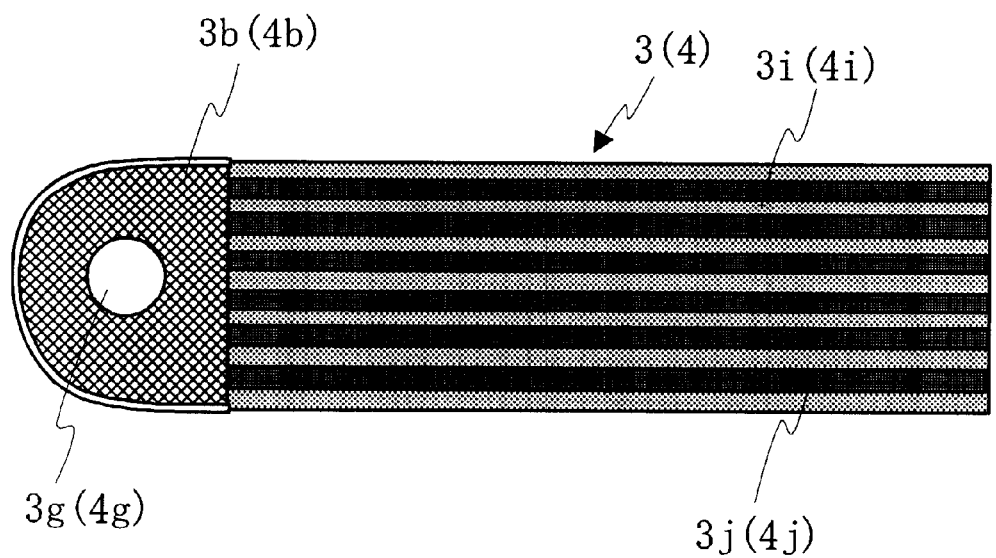
FIG. 39 is diagram showing other embodiment of the stretch band of the lumbago treating girdle according to the present invention.
Figure 40:
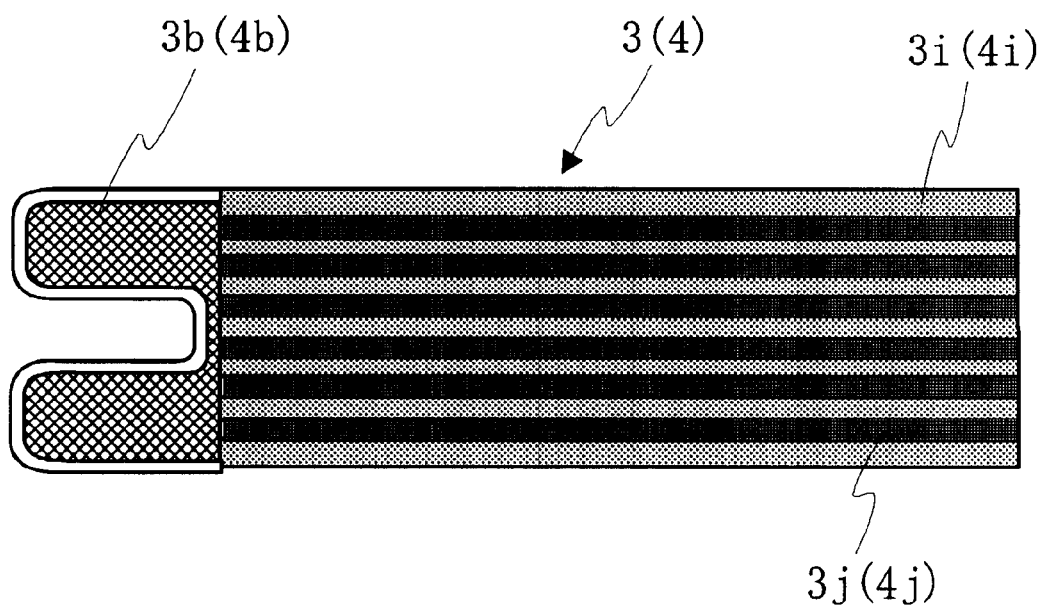
FIG. 40 is diagram showing other embodiment of the stretch band of the lumbago treating girdle according to the present invention.

BRIEF DESCRIPTION OF SYMBOLS 1 lumbago treating girdle
2 girdle main body
2a crotch portion
2b sewn portion
2c buttock portion
3 stretch band
3a left engaging member
3b left engaging piece
3c upper stretch band
3d lower stretch band
3e hemming member
3f engagement metal piece
3g through hole
3h base portion 3i stretch portion
3j mesh portion
4 stretch band
4a right engaging member
4b right engaging piece
4c upper stretch band
4d lower stretch band
4e hemming member
4f engagement metal piece
4g through hole
4h base portion
4i stretch portion
4j mesh portion
5 right femoral part
5a right leg passing port
6 left femoral part
6a left leg passing port
7 left engaging member
8 right engaging member
9 zipper
10 opening/closing metal piece
11 belt
12 press portion
12a left seam
12b right seam
13 opening/closing portion
13a opening/closing portion
14 lower opening/closing piece
14a engaging portion
15 upper opening/closing piece
15a engaging portion
16 cross band portion
16a left cross band
16b right cross band
17 left engaging member
17a right engaging member
17b lower engaging piece
17c lower engaging piece
17d upper engaging piece
17e upper engaging piece
18 engaging portion
18a engaging portion
19 horizontal band portion
19a horizontal band
19b engaging portion
20 left engaging member
20a right engaging member
20b lower engaging piece
20c lower engaging piece
20d upper engaging piece
20e upper engaging piece
20f engaging portion
20g engaging portion
21 engaging portion
21a engaging portion
22 left engaging member
22a right engaging member
22b engaging portion
22c engaging portion
23 shaping member
23a left vertical piece
23b right vertical piece
23c horizontal piece
24 slip preventing member
24a slip preventing member

What is claimed is:

1. A lumbago treating girdle comprising: a girdle main body including an inverse triangular press portion provided with a zipper extending in a vertical direction to a crotch portion from a belt disposed on an upper part of a front surface of the girdle main body, a portion sewn in a vertical direction on a back surface of the girdle main body, a right femoral part, a left femoral part, a left engaging member disposed on a left side of said press portion, and a right engaging member disposed on a right side of the press portion; a left stretch band which is attached to a middle of a left end portion of said girdle main body, and to a tip end of which a left engaging member with an engaging piece attached to one surface thereof is attached; and a right stretch band which is attached to a middle of a right end portion of said girdle main body, and to a tip end of which a right engaging member with an engaging piece attached to one surface thereof is attached, said left stretch band being attached to the girdle main body in such a manner that the left stretch band ascends toward the left, and said right stretch band being attached to the girdle main body in such a manner that the right stretch band ascends toward the right.

2. The lumbago treating girdle according to claim 1 wherein the left stretch band comprises an upper left stretch band and a lower left stretch band, and the right stretch band comprises an upper right stretch band and a lower right stretch band.

3. The lumbago treating girdle according to claim 1 or 2 wherein an opening/closing portion is disposed right above the crotch portion.

4. The lumbago treating girdle according to claim 1 or 2 wherein a cross band portion is disposed above the crotch portion.

5. The lumbago treating girdle according to claim 1 or 2 wherein a horizontal band portion is disposed above the crotch portion.

6. The lumbago treating girdle according to claim 1 or 2 wherein a shaping member is semen onto a back inner surface of the girdle main body.

7. A lumbago treating girdle comprising: a girdle main body including an inverse-triangular press portion provided with a zipper extending in a vertical direction to a crotch portion from a belt disposed on an upper part of a front surface of the girdle main body, a portion sewn in a vertical direction on a back surface of the girdle main body, a right femoral part and a left femoral part continuously disposed in left and right lower portions of said press portion, a left engaging member disposed on a left side of said press portion, a right engaging member disposed on a right side of said press portion, and an H-shaped shaping member disposed on a back inner side surface; a left stretch band which is attached to a middle of a left end portion of said girdle main body, to a tip end of which a left engaging member with an engaging piece attached to one surface thereof is attached, and in which a stretch portion and a mesh portion are alternately knitted; and a right stretch band which is attached to a middle of a right end portion of said girdle main body, to a tip end of which a right engaging member with an engaging piece attached to one surface thereof is attached, and in which the stretch portion and the mesh portion are alternately knitted, said left stretch band being attached to the girdle main body in such a manner that the tip end ascends toward the left, said right stretch band being attached to the girdle main body in such a manner that the tip end ascends toward the right.

8. The lumbago treating girdle according to claim 7 wherein a hemming member is attached to the tip ends of the left and right stretch bands, and an engaging metal is disposed on the tip ends of the left and right stretch bands.

9. The lumbago treating girdle according to claim 7 wherein the left and right stretch bands comprise upper and lower stretch bands, and a hemming member is attached to the tip ends of said left and right stretch bands.

10. The lumbago treating girdle according to claim 7 wherein a hemming member and left and right engaging pieces are attached to the tip ends of the left and right stretch bands, and base portions of said left and right stretch bands are sewn.

11. The lumbago treating girdle according to claim 7 wherein a hemming member and left and right engaging pieces are attached to the tip ends of the left and right stretch bands, and base portions of said left and right stretch bands are sewn.

12. The lumbago treating girdle according to claim 7 wherein the tip ends of the left and right stretch bands are formed into two forked parts, and a hemming member and left and right engaging pieces are attached to the tip ends of said left and right stretch bands.

* * * * *